(12) United States Patent
Lizio et al.

(10) Patent No.: US 8,765,152 B2
(45) Date of Patent: Jul. 1, 2014

(54) PHARMACEUTICAL OR NEUTRACEUTICAL FORMULATION

(75) Inventors: Rosario Lizio, Dieburg (DE); Michael Gottschalk, Ober-Ramstadt (DE); Michael Damm, Roedermark (DE); Norbert Windhab, Hofheim (DE); Melanie Liefke, Ober-Ramstadt (DE); Guenter Schmitt, Darmstadt (DE); Erna Roth, Darmstadt (DE); Ruediger Alexowsky, Nauheim (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 13/580,033

(22) PCT Filed: Feb. 25, 2010

(86) PCT No.: PCT/EP2010/052401
§ 371 (c)(1),
(2), (4) Date: Aug. 20, 2012

(87) PCT Pub. No.: WO2011/103920
PCT Pub. Date: Sep. 1, 2011

(65) Prior Publication Data
US 2012/0315334 A1   Dec. 13, 2012

(51) Int. Cl.
*A61K 9/00* (2006.01)
*A61K 9/16* (2006.01)
*A61K 38/00* (2006.01)
*A61K 38/11* (2006.01)
*A61K 48/00* (2006.01)
*A61K 31/70* (2006.01)
*A61K 31/727* (2006.01)

(52) U.S. Cl.
USPC ........... 424/400; 424/490; 514/1.1; 514/10.9; 514/44 R; 514/54; 514/56

(58) Field of Classification Search
USPC .......... 424/490, 400; 514/1.1, 10.9, 44 R, 54, 514/56
See application file for complete search history.

(56) References Cited

U.S. PATENT DOCUMENTS

| 2007/0026082 A1 | 2/2007 | Lizio et al. |
| 2008/0008764 A1 | 1/2008 | Milstein |
| 2008/0026051 A1* | 1/2008 | Lizio et al. ............ 424/452 |
| 2008/0274945 A1 | 11/2008 | Van Laere et al. |
| 2009/0238882 A1 | 9/2009 | Milstein |

FOREIGN PATENT DOCUMENTS

| CN | 1822821 A | 8/2006 |
| CN | 101484149 A | 7/2009 |
| JP | 2009-513553 | 4/2009 |
| JP | 2000-544639 | 12/2009 |
| WO | 90 01329 | 2/1990 |
| WO | 93 13753 | 7/1993 |
| WO | 2009/118722 | 10/2009 |
| WO | 2010/007515 | 1/2010 |

OTHER PUBLICATIONS

Trenktrog, T., et al., "Enteric coated insulin pellets: development drug release and in vivo evaluation," European Journal of Pharmaceutical Sciences, vol. 4, pp. 323-329, (1996).
International Search Report Issued Jun. 9, 2011 in PCT/EP10/52401 Filed Feb. 25, 2010.
Office Action as received in the corresponding Russian Patent Application No. 2012140651/15 (065607) dated Feb. 13, 2014 w/English Translation.
Office Action as received in the corresponding Japanese Patent Application No. 2012-554226 dated Jan. 20, 2014 (w/English Translation).

* cited by examiner

*Primary Examiner* — Blessing M Fubara
(74) *Attorney, Agent, or Firm* — Oblon, Spivak, McClelland, Maier & Neustadt, L.L.P.

(57) ABSTRACT

The invention relates to a pharmaceutical or nutraceutical formulation comprising a core, comprising an active pharmaceutical or nutraceutical ingredient, a penetration promoter and a bioavailability promoting agent, and a polymeric coating for the gastrointestinal targeted release of the active ingredient, characterized in that the bioavailability promoting agent is a pharmaceutically acceptable inhibitor of proteolytic enzymes, which increases the oral bioavailability of the active ingredient by a factor of at least five, compared to a corresponding formulation without the bioavailability promoting agent.

17 Claims, No Drawings

PHARMACEUTICAL OR NEUTRACEUTICAL FORMULATION

This application is a National Stage of PCT/EP10/052401 filed Feb. 25, 2010.

FIELD OF THE INVENTION

The invention relates to pharmaceutical or nutraceutical formulation comprising a core comprising an active pharmaceutical or nutraceutical ingredient, a penetration promoter, a bioavailability promoting agent which increases the bioavailability of the active ingredient and a polymeric coating for the gastrointestinal targeted release of the active ingredient.

TECHNICAL BACKGROUND

DE 19724458 A1 describes the use of proteolytic enzymes for the improvement of the absorption of pharmaceutical active ingredients.

EP 1302201 A1 describes pharmaceutical compositions improved in peroral absorbability. The composition comprises a drug, an aminoalkyl methacrylate copolymer E and an acidic substance.

EP 1466626 A1 describes medical compositions for improving oral absorption. The aminoalkyl methacrylate copolymer E is described therein as an agent for inhibiting the decomposition of a biological active peptide.

WO2005007139A2 describes an oral multiparticulate pharmaceutical form comprising pellets having a size in the range from 50 to 2500 μm, which are substantially composed of a) an inner matrix layer comprising an active substance which is a peptide or a protein, including derivatives or conjugates thereof, and is embedded in a matrix of a polymer having a mucoadhesive effect, where the matrix may optionally comprise further pharmaceutically usual excipients, b) an outer film coating consisting essentially of an anionic polymer or copolymer which may optionally be formulated with pharmaceutically usual excipients, especially plasticizers, characterized in that the multiparticulate pharmaceutical form is formulated so that the contained pellets are released in the pH range of the stomach, the outer coating is adjusted through the choice of the anionic polymer or copolymer or its formulation with excipients and its layer thickness such that the coating dissolves in pH ranges from 4.0 to 8.0 in the intestine within 15 to 60 min, so that the active substance-containing, mucoadhesive matrix layer is exposed, and can bind to the intestinal mucosa and release the active substance there, where the polymer having a mucoadhesive effect is chosen so that it exhibits a mucoadhesive effect of $\eta_b$=150 to 1000 mPa·s and a water uptake of from 10 to 750% in 15 min in a range of +/−0.5 pH units relative to the pH at which the outer coating starts to dissolve, and the active substance content of the matrix layer is a maximum of 40% by weight of the content of polymer having a mucoadhesive effect.

It is mentioned that the mucoadhesive matrix layer may contain further excipients such as protease inhibitors, for instance a soybean trypsin inhibitor, or penetration promoters. However it is suggested to use penetration promoters only in combination with high molecular weight ($M_w$) active ingredients such as proteins with a $M_w$ of 10.000 or more. Protease inhibitors may be used in combination with proteins or peptides with a $M_w$ of 3.000 to 10.000 and stabilizers such as fatty acids or fatty alcohols which form a lipophilic matrix. There are no concrete examples in which protease inhibitors and penetration promoters are combined.

EP 1771157 B1 describes a multiparticle pharmaceutical dosage form for a low-soluble active substances and method for producing said pharmaceutical dosage form.

WO 2006/061069 A1 describes a multiparticle form of administration comprising nucleic acid containing mucoadhesive active ingredients and methods for producing said forms of administration.

The Bowman-Birk inhibitor (BBI) is a well known designation of a family of stable low molecular weight trypsin and chymotrypsin inhibitors found in soybeans and various other seeds, mainly in leguminous seeds and vegetable materials. See for instance U.S. Pat. No. 5,962,414 or U.S. Pat. No. 6,767,564.

U.S. Pat. No. 6,767,564 B2 describes the use bowman birk inhibitor (BBI) for the treatment of multiple sclerosis and other autoimmune diseases such as Guillian Barre Syndrome and rheumatoid arthritis. It is mentioned that orally ingested bowman birk inhibitor is absorbed and has systemic effects. Approximately 50% of the ingested bowman birk inhibitor is absorbed in to the bloodstream. It is further mentioned that bowman birk inhibitor concentrate (BBIC), a soybean derived extract enriched in the protease inhibitor, is reportedly a better inhibitor of human chymases than any other physiologic protease inhibitor described to date.

Problem and Solution

During their studies the inventors have found that pharmaceutical or nutraceutical formulations comprising a core, comprising an active pharmaceutical or nutraceutical ingredient, a penetration promoter and a polymeric coating for the gastrointestinal targeted release of the active ingredient gave good cell penetration effects in in-vitro cell assays.

However the promising results obtained with the active ingredient desmopressin in vitro lead only to disappointing results in vivo. When the corresponding formulations were tested in-vivo in minipigs only pour bioavailability, measured in-vivo as the plasma concentration levels, could be detected.

Since desmopressin is a peptide the addition of a proteolytic enzyme inhibitor which could prevent enzymatic degradation of the peptide by pancreatic enzymes in-vivo was tested first in-vitro and then in-vivo. In the in-vitro assay in the presence of a pancreatic enzyme cocktail containing different peptidases and proteinases a certain protecting effect of the addition of the Bowman-Birk inhibitor (BBI) as proteolytic enzyme inhibitor was observed. It was expected to find this effect on the same level or somewhat lower in the in-vivo system.

However to the great surprise of the inventors the in-vivo effect of the addition of the Bowman-Birk inhibitor was more than five times respectively almost ten times higher than expected. Due to the fact that the in-vivo effect was so much higher compared to the in-vitro results the inventors show that this effect can not be explained merely by the protective effect of the proteolytic enzyme inhibitor against the pancreatic enzymes. Furthermore there seems to be a new unknown effect that increases the bioavailability of active ingredients caused by the addition of a proteolytic enzyme inhibitor in general or at least by such one from plant origin or at least by the Bowman-Birk inhibitor in combination with the other elements of the system as claimed. Thus the inventors believe that the pharmaceutical or nutraceutical formulation as claimed will be applicable to other active ingredients which are not peptides or proteins as well.

It was one object of the present invention to provide a pharmaceutical or nutraceutical formulation comprising an active pharmaceutical or nutraceutical ingredient for oral applications with increased bioavailability.

The problem was solved by a pharmaceutical or nutraceutical formulation comprising a core, comprising an active pharmaceutical or nutraceutical ingredient, a penetration promoter and a bioavailability promoting agent, and a polymeric coating for the gastrointestinal targeted release of the active ingredient, characterized in that, the bioavailability promoting agent is a pharmaceutically acceptable inhibitor of proteolytic enzymes, which increases the oral bioavailability of the active ingredient by a factor of at least five, compared to a corresponding formulation without the bioavailability promoting agent.

DETAILED DESCRIPTION

Pharmaceutical or Nutraceutical Formulation

The invention relates to a pharmaceutical or nutraceutical formulation comprising a core comprising an active pharmaceutical or nutraceutical ingredient, a penetration promoter, a bioavailability promoting agent which increases the oral bioavailability of the active ingredient and a polymeric coating for the gastrointestinal targeted release of the active ingredient.

In a simple embodiment the pharmaceutical or nutraceutical formulation is a coated matrix tablet. However it is preferred that pharmaceutical or nutraceutical formulation is multiparticulate formulation.

Multiparticulate Pharmaceutical or Nutraceutical Formulation

The invention relates preferably to a multiparticulate pharmaceutical or nutraceutical formulation comprising a multitude of particles in one dosage unit. The particles are preferably coated or uncoated pellets.

Preferred particles sizes may be 0.2 to 2, preferably 0.3 to 1 mm. The comparative small particle size has the advantage that there is at least in the case of coated pellets a rapid and sure transfer from the stomach to the duodenum. In all cases there is the advantage of a high standardization of the active ingredient dosage and good distribution in the intestine.

A multiparticulate pharmaceutical or nutraceutical formulation may contain 10 to 1000, preferably 50 to 500 particles which preferably coated or uncoated pellets.

The medicament in multilayer form of the present invention makes primarily sense as a multiparticulate pharmaceutical or nutraceutical form.

The multiparticulate form may be for instance a pellet-containing tablet or compressed tablet, a minitablet, a sachet or a capsule filled with a plurality of active ingredient containing particles or pellets.

All these terms are well known to a skilled person in field of pharmacy and galenics.

The term pellet-containing tablet or compressed tablet is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term minitablet is well known to the skilled person. A minitablet is smaller than the traditional tablet and may have a size of around 1 to 4 or less than 5 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The term capsule is well known to the skilled person. A capsule is like the sachet a container for pellets containing liquids or also dry pellets or powders. However in contrast to the sachet the capsule consists of pharmaceutically acceptable excipients such as gelatine or hydroxypropylmethylcellulose and is intended to be ingested like a tablet. The capsules disrupts after oral ingestion and contact with the gastric or intestinal fluids and the contained multiple units are set free. Capsules for pharmaceutical purposes are commercially available in different standardized sizes.

Pellets

Pellets comprise a core, comprising an active pharmaceutical or nutraceutical ingredient, a penetration promoter and a bioavailability promoting agent which increases the bioavailability of the active ingredient. The core may preferably have a coating for the gastrointestinal targeted release of the active ingredient (enteric coating). For instance a hydroxypropylmethylcellulose (HPMC) or a gelatine capsule may be filled with a multitude of enteric coated pellets.

If the pellets do not have a coating for the gastrointestinal targeted release of the active ingredient, then the dosage unit must comprise such a polymeric coating. For instance a HPMC or a gelatine capsule may contain pellets without an enteric coating but the capsule itself is then coated with an enteric polymer. Enteric coating of capsules, especially of HPMC capsules is for instance known from EP 1117386 A1.

The average particle diameter of coated or uncoated pellet sizes may range from 100-1500 μm, preferably from 200 to 800 μm.

Preferred the pellets are consisting of a core, comprising an active pharmaceutical or nutraceutical ingredient, a penetration promoter, a bioavailability promoting agent and optionally an enteric coating.

Most preferred the pellets are consisting of a core essentially consisting of an active pharmaceutical or nutraceutical ingredient, a penetration promoter, a bioavailability promoting agent which increases the oral bioavailability of the active ingredient, a separating or synchronisation layer and an enteric coating. This preferred form is reduced to its essential elements with the advantage of reducing the number of excipients, which is always of advantage since the risks of interactions with the active ingredient or possible intolerances for the patient are reduced.

Preferred the pellets, particles or cores do not contain any or any essential amounts of polymers having a mucoadhesive effect. An essential amount of a polymer having a mucoadhesive effect is approximately more than 10% by weight in the final formulation. Preferred the particles do not contain any or any essential amounts of mucoadhesive polymers that exhibit a mucoadhesive effect of $\eta_b$=150 to 1000, preferably 150 to 600 mPa·s and a water uptake of from 10 to 750, preferably 10 to 250, particularly preferably 10 to 160% in 15 min in a range of +/−0.5, preferably +/−0.3 pH units relative to the pH at which the outer coating starts to dissolve. Preferred the particles do not contain any or any essential amounts of a chitosan or a (meth)acrylate copolymer consisting of 20-40% by weight methyl methacrylate and 60 to 80% by weight methacrylic acid or sodium carboxymethylcellulose or a crosslinked and/or uncrosslinked polyacrylic acid or a lectin or a sodium alginate or a pectin.

Measurement of the Mucoadhesive Properties

A suitable measurement method for characterizing mucoadhesive properties is contained in Hassan and Gallo (1990) (see Hassan E. E. and Gallo J. M. "A Simple Rheological Method for the in Vitro Assessment of Mucin-Polymer Bioadhesive Bond Strength" Pharma Res. 7(5), 491 (1990)). The method is based on the assumption that the viscosity ($\eta$, dynamic viscosity or viscosity coefficient) of a mixture of polymers with mucin is different from the total of the viscosities of the individual components. The relationship applying is $\eta_{mixture\ of\ polymer\ with\ mucin} = \eta_{mucin} + \eta_{polymer} + \eta_b$, where $\eta_b$ stands for the difference. A higher $\eta_b$ means greater mucoadhesive properties. The individual components are initially measured for their viscosity using a rotational viscometer. A 0.5% strength (w/w) aqueous solution of the mucoadhesive polymer and a 15% strength solution of porcine gastric mucin are employed. To determine the mucoadhesive properties $\eta_b$, mucin and polymer are measured alone and mixed in the stated concentrations.

Hydration and Water Uptake

The hydration of polymers is based on the affinity of the polymer to take up water. Polymers swell owing to this water uptake. This is concerned with an imbalance between the chemical potential of the water in the polymer and the water in the surrounding medium. The water is taken up, owing to the osmotic pressure of the polymer, until an equilibrium is set up between inner and outer phase. The polymer is then 100% hydrated. Polymers having a low average molecular weight are then in the form of a solution. A gel is produced with polymers having a higher molecular weight or with crosslinked polymers. The water uptake until the equilibrium is set up may amount for example to up to 10 times the inherent weight, corresponding to 1000% of the polymer weight.

Measurement of the Percentage Water Uptake

Measurement of the percentage water uptake is familiar to the skilled worker. A suitable method is described for example in the Lehrbuch der pharmazeutischen Technologie/Rudolf Voigt, Basel: Verlag Chemie, 5$^{th}$ completely revised edition, 1984, page 151, 7.7.6 under "Aufsaugvermögen". The method makes use of the so-called Enslin apparatus, in which a glass suction filter funnel is connected by tubing to a graduated pipette. The pipette is mounted exactly horizontally in such a way that it is at the same level as the glass frit. A water uptake of 100% is defined in the present case as a water uptake of 1 ml of water per 1 g of polymer having a mucoadhesive effect in 15 min.

Core

The core is comprising an active pharmaceutical or nutraceutical ingredient, a penetration promoter and a bioavailability promoting agent which increases the bioavailability of the active ingredient. The core may comprise further pharmaceutically or nutraceutically excipients which are different from the active pharmaceutical or nutraceutical ingredient, the penetration promoter and the bioavailability promoting agent. The core may further comprise optionally a synchronisation layer.

The core may comprise a neutral core particle (non-pareil) on which the active pharmaceutical or nutraceutical ingredient, the penetration promoter and the bioavailability promoting agent are applied for instance by spraying techniques, preferably bound in a binder like for instance lactose or polyvinylpyrrolidone. However, preferably the core does not comprise a neutral core particle (non-pareil).

Preferably the core comprises, is essentially comprising or contains the active pharmaceutical or nutraceutical ingredient, the penetration promoter and the bioavailability promoting agent. Preferably the core is in the form of a spherical pellet which may be produced by known methods like wet extrusion, melt extrusion, rotagglomeration or spheronization. The core may contain the active pharmaceutical or nutraceutical ingredient, the penetration promoter and the bioavailability promoting agent in the form of a matrix structure or in the form of a layer structure. A layer structure may be generated or applied by known spray coating techniques.

The active pharmaceutical or nutraceutical ingredient, the penetration promoter and the bioavailability promoting agent may be mixed together to form a unique matrix structure.

The core in total may contain up to 90, up to 50, up to 30, up to 20, up to 10% by weight of further excipients. Preferably the core does not contain essential amounts or any further excipients.

The core may further comprise a synchronisation layer.

The core may be further coated by a polymeric enteric coating for the gastrointestinal targeted release of the active ingredient.

The core may be further coated by a synchronisation layer and by a polymeric coating for the gastrointestinal targeted release of the active ingredient.

The core, if coated or not, may be further coated with a rapidly dissolving top coat comprising a binder like sugar and for instance a pigment.

Specific Galenic Approach for Anionic Active Ingredients

In the case where the active pharmaceutical or nutraceutical ingredient is anionic and the penetration promotor is cationic, unwanted interactions, such as precipitation or inactivation of the penetration properties of the penetration promoter, may occur when the substances are mixed together in amounts which are approximately equimolar in respect to their charges or where the active ingredient is present in access over the penetration promoter.

In order to avoid such undesired interactions the active pharmaceutical or nutraceutical ingredient and the penetration promoter may be separated in separate layers (layered core structure). The individual layers may contain further excipients, which are different from the active pharmaceutical or nutraceutical ingredient, the penetration promoter and the bioavailability promoting agent, such as binders for instance polyvinyl pyrrolidone or lactose or polymers such as celluloses or (meth)acrylic copolymers.

A further approach to avoid precipitation or inactivation of the penetration properties of the penetration promoter may be to use the matrix structure but with the addition of excipients which weaken the undesired ionic interactions, such as salts, such as sodium chloride, potassium chloride, Mg-stearate or the like, amphiphilic polymers or hydrogene bonding non-ionic polymers.

Thus the inventive formulation may be further characterized in that the active ingredient is anionic and the penetration promotor is cationic and that ionic interactions between both components are avoided either

- by an excessive amount of the penetration promotor in a mixture of both components in the same compartment of the formulation or
- by local separation of both components in different compartments of the formulation or
- by the addition of salts, amphiphilic polymers or hydrogen bonding non-ionic polymers to a mixture of both components in the same compartment of the formulation.

The term compartments of the formulation are meant in the sense of the core with a homogeneous matrix structure comprising the active ingredient and the penetration promotor (mixture of both components in the same compartment) or the core with the active ingredient and separate layer which may contain the penetration promotor or vice versa (local separation in different compartments).

Amounts of the Main Components in the Final Formulation

The amount of the penetration promotor in the final formulation, which means the total single dosage to be ingested, may be in the range of 1 to 60% by weight, preferably 10 to 40% by weight.

If the penetration promotor is also a polymer with a mucoadhesive effect, like chitosan, the amount in the final formulation should not exceed 10% by weight to avoid that formulation becomes mucoadhesive. Thus polymers with a mucoadhesive effect, like chitosan, should preferably be combined with penetration promotors without such a mucoadhesive effect, like EUDRAGIT® E for instance, if amounts of more than 10% by weight of penetration promotors are required to ensure a sufficient penetration promotor effect.

The certain amount should be chosen in order to preferably obtain a final concentration in the relevant physiological liquids, for instance 100 ml intestinal fluid, between 0.1 to 2.5 mg/ml, preferably 0.5 to 1 mg/ml. This should correspond to a transepithelial electrical resistance (TEER-value) of Caco-II-cells in an in-vitro test system of 50% or less, preferably of 40% or less, preferably of 30% or less, preferably of 20% or less in the presence of the penetration promotor at a concentration of 1 mg/ml after 30 min measured in a transport experiment using desmopressin as active agent and a Caco-2-cell monolayer culture as transport barrier.

The amount of the bioavailability promoting agent in the final formulation, which means the total single dosage to be ingested, may be in the range of 0.1 to 10% by weight, preferably 0.5 to 5% by weight most preferably 1 to 2.5% by weight. The certain amount should be chosen in order to preferably obtain a final concentration in the relevant physiological liquids, for instance 100 ml intestinal fluid, between 0.004 to 0.1 mg/ml, preferably 0.02 to 0.04 mg/ml. This should correspond to an increase of the oral bioavailability of the active ingredient by a factor of at least five, compared to a corresponding formulation without the bioavailability promoting agent.

The amount of the active pharmaceutical or nutraceutical ingredient in the formulation is very variable depending on the therapeutically required amount. As an example to total therapeutically required amount of desmopressin is about 200 μg per dosage form whereas the total therapeutically required amount of heparin may be about 200 mg per dosage form.

Active Pharmaceutical or Nutraceutical Ingredient

The active ingredient may be any active pharmaceutical or nutraceutical ingredient where peroral delivery is desirable. Preferably the active ingredient belongs to the group of BCS-classes III and IV, where an improvement of the oral absorption is desirable. Preferably the active ingredient is a molecule of biological origin, for instance a protein or a peptide, a nucleic acid, a lipid or a carbohydrate or a natural or synthetical derivative of these substances.

The active ingredient may be a protein or a peptide having an average molecular weight $M_w$ of less than 3000 Da. Examples of such peptides are in particular abarelix, angiotensin II, anidulafungin, antide, argipressin, azaline and azaline B, bombesin antagonist, bradykinin, buserelin, cetrorelix, cyclosporine A, desmopressin, detirelix, encephalins (Leu-, Met-) ganirelix, gonadorelin, goserelin, growth hormone secretagogue, micafungin, nafarelin, leuprolide, leuprorelin, octreotide, orntide, oxytocin, ramorelix, secretin, somatotropin, terlipressin, tetracosactide, teverelix, triptorelin, thyroliberin, thyrotropin, vasopressin.

The active ingredient may be a protein or peptide having an average molecular weight $M_w$ of from 3000 to 10 000 Da. Examples of such proteins or peptides are in particular calcitonin, corticotrophin, endorphins, epithelial growth factor, glucagon, insulin, novolin, parathyroid hormone, relaxin, pro-somatostatin, salmon secretin.

The active ingredient may be a protein or peptide having an average molecular weight $M_w$ of more than 10 000. Examples of such proteins or peptides are in particular interferons (alpha, beta, gamma), interleukins (IL1, IL2), somatotropin, erythropoietin, tumor necrosis factor (TNF alpha, beta), relaxin, endorphin, domase alpha, follicle stimulating hormone (FSH), human chorion gonadotropin (HCG), human growth hormone release factor (hGRF), luteinizing hormone (LH) or epidermal growth factor.

The active ingredient may be desmopressin or a derivative thereof like different salts or desmopressin acetate or desmopressin lactate.

The active ingredient may be is a polysaccharide. The active ingredient may be a heparin or a derivative thereof like unfractionated heparins or mid molecular weight heparins and low molecular weight heparins or very low molecular weight heparins.

The active ingredient may be a nucleic acid or derivative thereof like for example 5-Fluoro-Uracil.

Examples for nutraceutical active ingredients are vitamins, essential fatty acids, resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or anthocyanins from berries.

Further examples for nutraceuticals are vitamins and minerals, taurine, Omega-3, green tea catechins, co-enzyme Q10, Aloe vera, glucosamine, chondroitin, whey protein, guarana, gingko, gamma amino butyric acid. Other nutraceuticals can be chosen from the classes of botanicals, probiotics, prebiotics, plant sterols and enzymes.

BCS Classes III and IV

The active ingredient(s) may belong, for example, to the group of BCS classes III and IV (Biopharmaceutical classification system according to Prof. Amidon; Amidon et al., Pharm. Res. 12, 413-420 (1995)) and/or from the group of the antiandrogenics, antidepressives, antidiabetics, antirheumatics, glucocorticoids, cytostatics, migraine drugs, neuroleptics, antibiotics, oestrogens, vitamins, psychotropic drugs, ACE inhibitors, β-blockers, calcium channel blockers, diuretics, cardiac glycosides, antiepileptics, diuretics/antiglaucoma, uricostatics, $H_2$ receptor blockers and virustatics.

The Pharmaceutical or nutraceutical formulation comprises at least one, generally only one, active ingredient, but if appropriate also combinations of two or more active ingredients. The active ingredient present may therefore consist of a single active ingredient or if appropriate also of a plurality of individual active ingredients.

BCS Class III—Low Permeability, High Solubility

The absorption is limited by the permeation rate but the drug is solvated very fast.

BCS Class IV—Low Permeability, Low Solubility

Those compounds have a poor bioavailability. Usually they are not well absorbed over the intestinal mucosa and a high variability is expected.

The active ingredient(s) of BCS classes III and IV has/have preferably a permeability which is less than 90% of the administered dose based on a mass-balance determination or in comparison to and intravenous dose. Permeability is based indirectly on the extent of absorption of a drug substance in humans and directly on the measurement of rates of mass transfer across human intestinal membrane. Alternatively non-human systems capable of prediction the drug absorption systems capable of predicting the drug absorption in humans can be used (such as in-vitro culture methods). A drug substance is considered highly permeable when the extent of absorption in humans is determined to be 90% or more of the administered dose based on a mass-balance determination or in comparison to and intravenous dose.

The active ingredients of BCS class IV may have a solubility in demineralized water of 3.3 g/l or less. The active ingredients of BCS class III have good solubility in water. The active ingredients of BCS class IV have a low permeability. The advantages of the invention are therefore displayed in particular for the active ingredients of BCS class III, since the permeability of the active ingredient here constitutes the sole limitation of its bioavailability. However, increased permeability of the active ingredient can also be helpful in the case of active ingredients of BCS class IV, in order to achieve a certain improvement in the bioavailability at least gradually in spite of the limitation of poor solubility in water of these active ingredients.

The active ingredient(s) may be bicalutamide, anastrozole, albendazole, amitryptiline, artemether, chlorpromazine, ciprofloxacin, clofazimine, dapsone, diloxanide, efavirenz, folic acid, furosemide, glibenclamide, griseofulvin, haloperidol, ivermectin, ibuprofen, idinavir, lopinavir, lumefantrin, mebendazole, mefloquin, niclosamide, nelfinavir, nifedipine, nitrofurantoin, phenyloin, pyrantel, pyremethamine, retinol, ritonavir, spironolactone, sulfadiazine, sulfasalazine, sulfamethoxazole, triclabendazole, trimethoprim, valproic acid, verapamil, warfarin, nalidixic acid, nevirapine, praziquantel, rifampicin, glimipiride, nilutamide, bromocriptine, ketotifen, letrozole, naratriptan, ganciclovir, orlistat, misoprostol, granistron, pioglitazone, lamivudine, rosiglitazone, zidovudine, enalapril, atenolol, nadolol, felodipine, bepridil, digoxin, digitoxin, carbamazepine, acetazolamide, allopurinol, cimetidine, ranitidine or oxcarbazepine.

Solubility in Water

The active ingredients may have a solubility in demineralized water of 3.3 g/l or less, preferably 3.3 g/l or less, in particular 1.1 g/l or less.

The solubility in water for the active ingredient can be defined according to DAB 10 (Deutsches Arzneibuch [German Pharmacopoeia], 10th edition with 3rd revision 1994, Deutscher Apothekerverlag, Stuttgart and Govi Verlag, Frankfurt am Main, 2nd revision (1993), IV Allgemeine Vorschriften [IV General methods], p. 5-6, "Loslichkeit and Lösungsmittel" ["Solubility and solvents"]; see also Ph. Eur. 4.07, 2004).

Inhibitor of Enzymatical Degradation of the Active Ingredient

When the active ingredient is a molecule of biological origin, for instance a protein or a peptide, a nucleic acid, a lipid or a carbohydrate or a natural or synthetical derivative of these substances, an inhibitor may be added that prevents or reduces of the enzymatical degradation of the active ingredient, which may occur under in the environmental conditions of the gastrointestinal tract. The inhibitor is different from the bioavailability promoting agent and thus may be added in addition. Preferably such an inhibitor which prevents or reduces the enzymatical degradation of the active ingredient should be more or less specific for the active ingredient of biological origin. Preferably the inhibitor that prevents or reduces of the enzymatical degradation of the active ingredient should be pharmaceutically acceptable in relation to the certain application in animals or in humans. Pharmaceutically acceptable could be defined in the sense that a generally recognized as safe status (GRAS) or something comparable to the GRAS status exists.

In the case that the active ingredient is a protein or a peptide which is mainly a substrate of trypsin or chymotrypsin there is normally no need to add an inhibitor of proteolytic enzymes since the bioavailability promotor is already such an inhibitor. However it is not excluded that a further proteolytic enzyme may be added in the case other proteolytic enzymes are responsible for the degradation, although it is preferred that apart from the bioavailability promotor there is no further inhibitor of proteolytic enzymes present in the formulation.

In the case that the active ingredient is a nucleic acid, preferably a DNA or a RNA, the inhibitor of enzymatical degradation is a DNAse- or RNAse-inhibitor, preferably DNAse- or RNAse-inhibitors from mammalian animal or from human sources.

In the case that the active ingredient is a glycosidic substance, preferably a sulfonated or a non-sulfonated glucosaminoglycane, like for instance a proteoglycan, a heparine or a heparansulfate, the inhibitor of enzymatical degradation may be an inhibitor of heparanase (EC. 3.2.1.B2) or a heparine lyase (EC. 4.2.2.7) or heparinsulfate lyase (EC. 4.2.2.8). Further inhibitors may be the inhibitor of L-Iduronidase (EC 3.2.1.76), N-sulfoglucosamine-3-sulfatase (EC 3.1.6.15), iduronate-2-sulfatase (EC 3.1.6.13), heparan-alpha-glucosaminide N-acetyltransferase (EC 2.3.1.78), alpha-und beta amylase (EC 3.2.1.1, EC 3.2.1.2), glucan 1,4-alpha-glucosidase (EC 3.2.1.3), alpha,alpha-trehalase (EC 3.2.1.28) or sucrose alpha-glucosidase (EC 3.2.1.48).

Heparanases (EC. 3.2.1.B2) are endogenic enzyms which can specificly cut heparansulfate-chains from cell surfaces and basal membrane-heparanesulfate-proteoglycanes.

Examples of inhibitor of enzymatical degradation of heparanase are polyphenols, preferably from the groups of stilbenes, flavonoides or anthocyanes. Preferred is resveratrol (trans-3,4,5-trihydroxystilbene) which can be isolated for instance from *Polygonum cuspidatum* or from grape vine. The inhibitory effect of resveratrol on heparanase has been shown for instance by Ahn et. al. (2006) *Life Sciences* 79, 1661-1665.

Penetration Promoter

A penetration promoter is the sense of the present invention decreases the trans epithelial electrical resistance (TEER-values) of Caco-II-cells in an in-vitro test system.

Preferably the penetration promoter in the sense of the present invention may be defined by reducing the initial TEER-value of the buffer solution without penetration promotor (100%) to 50% or less, preferably 40% or less, preferably 30% or less, preferably 20% or less in the presence of the penetration promotor at a concentration of 1 mg/ml after 60 min measured in a a Caco-2-cell monolayer culture as transport barrier. The method of testing TEER-values in a transport experiment using a Caco-2-cell monolayer culture respectively through a Caco-2-cell monolayer culture barrier is well established and known to a person skilled in the art.

For the avoidance of doubt the outlining conditions as also used in example 12 may be summarized here: Caco-2 passage number less than 50; Culture age 14 to 30 days on Transwell™ filters; TEER values before and after transport above 200 $\Omega \cdot cm^2$ (indicating integrity and tightness of the cell monolayer); apparent permeability coefficient (apical/basolateral and basolateral/apical (ab and ba)) of a low permeable marker (Fluorescein) less than $1 \cdot 10^{-6}$ $cm \cdot s^{-1}$ (indicating suitability of the model to identify low permeable transport, assuring tightness of the cell monolayer); Apparent permeability coefficient (ba) of Rhodamine 123 higher than $4 \cdot 10^{-6}$ $cm \cdot s^{-1}$ (indicating evident expression of P-glycoprotein); Apparent permeability coefficient (ab) of propranolol higher than $5 \cdot 10^{-6}$ $cm \cdot s^{-1}$ (indicating suitability of the model to identify high permeable transport); buffers which may be used in the transport experiments for the apical or for the basolateral side are HBSS buffer pH 6.5 to 7.4 for the apical side and HBSS buffer pH 7.4 for the basolateral side (pH adjusted individually); Cell culture medium: Dulbecco's Modified Eagle Medium (DMEM) preferably supplemented with non-essential amino acids and gentamycin sulfate as known in the art.

Preferred the penetration promoter is a polymeric substance or more preferred a cationic polymeric substance.

Preferred the penetration promoter may be a cationic (meth)acrylate copolymer comprising tertiary amino groups.

Most preferred the penetration promoter may be a copolymer composed of 30 to 80% by weight of $C_1$- to $C_4$-alkyl esters of acrylic or of methacrylic acid, and 70 to 20% by weight of alkyl(meth)acrylate monomers having a tertiary amino group in the alkyl radical.

Penetration promoters which may be excluded are in particular plasticizers such as, for example, triethyl citrate, acetyl triethyl citrate, diethyl sebacate, dibutyl sebacate, polymers such as carbomer, sodium carboxymethylcellulose, polycarbophil-cysteines, long-chain fatty acids, their esters (for example mono and diglycerides) and their salts such as lauric acid, laurinsulfonic acid, palmitic acid, caprylic acid, capric acid, oleic acid, acylcarnitines, chelating agents such as EDTA, salicylates, cyclodextrins, polyacrylic acids, bile acids such as cholic acid, cholyltaurine, cholylsarcosine, chenodeoxycholic acid and their salts such as Na cholate, Na glycocholate, Na taurocholate, Na taurodihydrofusidate, Na glycodihydrofusidate, surfactants and emulsifiers such as, in particular, sodium dodecylsulfate (SDS), polysorbate 80 (Tween 80), polyethoxylated castor oil (Cremophor EL), the toxin zonula occludens toxin (ZOT) and vitamins such as vitamin E (tocopherol) or vitamin B12.

EUDRAGIT® E Type

The cationic (meth)acrylate copolymer comprising tertiary amino groups.

may be composed partly or fully of alkyl acrylates and/or alkyl methacrylates having a tertiary amino group in the alkyl radical. Suitable (meth)acrylate copolymers are known, for example, from EP 0 058 765 B1.

The cationic (meth)acrylate copolymer comprising tertiary amino groups may be composed, for example, of 30 to 80% by weight of free-radically polymerized $C_1$- to $C_4$-alkyl esters of acrylic acid or of methacrylic acid, and 70 to 20% by weight of (meth)acrylate monomers having a tertiary amino group in the alkyl radical.

Suitable monomers with functional tertiary amino groups are detailed in U.S. Pat. No. 4,705,695, column 3 line 64 to column 4 line 13. Mention should be made in particular of dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethyl)propyl methacrylate, (3-diethylamino-2,2-dimethyl)propyl acrylate and diethylamino-2,2-dimethyl)propyl methacrylate. Particular preference is given to dimethylaminoethyl methacrylate.

The content of the monomers with tertiary amino groups in the copolymer may advantageously be between 20 and 70% by weight, preferably between 40 and 60% by weight. The proportion of the $C_1$- to $C_4$-alkyl esters of acrylic acid or methacrylic acid is 70-30% by weight. Mention should be made of methyl methacrylate, ethyl methacrylate, butyl methacrylate, methyl acrylate, ethyl acrylate and butyl acrylate.

A suitable (meth)acrylate copolymer with tertiary amino groups may be formed, for example, from 20-30% by weight of methyl methacrylate, 20-30% by weight of butyl methacrylate and 60-40% by weight of dimethylaminoethyl methacrylate.

A specifically suitable commercial (meth)acrylate copolymer with tertiary amino groups is, for example, formed from 25% by weight of methyl methacrylate, 25% by weight of butyl methacrylate and 50% by weight of dimethylaminoethyl methacrylate (EUDRAGIT® E100 or EUDRAGIT® E PO (powder form)). EUDRAGIT® E100 and EUDRAGIT® E PO are water-soluble below approx. pH 5.0 and are thus also gastric juice-soluble.

The penetration promoter may be a may be a so called "amino methacrylate copolymer (USP/NF)", "basic butylated methacrylate copolymer (Ph. Eur)" or "aminoalkyl methacrylate copolymer E (JPE)" which are of the EUDRAGIT® E type.

Use of carbonated amino(meth)acrylate copolymer

The penetration promoter which is an amino(meth)acrylate copolymer, a cationic (meth)acrylate copolymer comprising tertiary amino groups, may be advantageously applied to the core in the form of an aqueous medium carbonated with carbon dioxide for instance by spray coating. Thus it becomes possible to add the penetration promoter to the formulation of the cores, which may have a matrix structure or a layered structure, whereby the penetration promoter in the matrix or in a layer around the core does not contain any traces of acids.

It was found that an aqueous medium carbonated with carbon dioxide may be used to realize a solution or a dispersion of an amino(meth)acrylate copolymer. It has been demonstrated that the amino groups are at least partially neutralized by the carbonic acid/hydrogen carbonate dissolved in the aqueous phase and thus the amino(meth)acrylate copolymer becomes at least dispersed, partially dissolved or even completely dissolved or something in between these conditions.

The amino(meth)acrylate copolymer containing carbonated aqueous medium can be easily handled in a similar way like organic solvent solutions. However in this case not the organic solvent is removed but the carbonated water. This means that a dried coating made from the inventive dispersion or solution will consist more or less of the pure amino(meth) acrylate polymer or copolymer since the carbon dioxide is removed with the vapour. This is a striking advantage over the aqueous dispersions which are partially neutralized by solid or liquid acids, where the acids or other excipients always remain with the dried amino(meth)acrylate copolymer formulation.

Thus it is advantageous to use an aqueous medium containing an amino(meth)acrylate copolymer which is not soluble in demineralised water, where the medium may have a content of the aqueous phase of at least 60% by weight and a content of solids of up to 40% by weight comprising the amino(meth)acrylate copolymer, whereby the aqueous phase is charged by a sufficient amount of carbon dioxide that effects the amino(meth)acrylate copolymer to be present in solute form in the medium.

Bioavailability Promoting Agent

The bioavailability promoting agent is a pharmaceutically acceptable inhibitor of proteolytic enzymes, which increases the oral bioavailability of the active ingredient by a factor of at least five, compared to a corresponding formulation without the bioavailability promoting agent.

The bioavailability promoting agent is a pharmaceutically acceptable inhibitor of proteolytic enzymes, preferably an inhibitor of trypsin and chymotrypsin.

An inhibitor of proteolytic enzymes may be defined within the borders of the enzyme inhibition experiments of example 14. Thus an inhibitor of proteolytic enzymes in the sense of the invention may be defined as such an inhibitor which at a concentration not exceeding 1 mg/ml prevents an initial amount of a 20 µg desmopressin acetate/ml solution in HBSS buffer pH 6.5 at 37° C. and an incubation time of 180 minutes to be reduced to less than 80% in the presence of a pancreatin solution with a concentration of 10 mg/ml.

The bioavailability promoting agent is a pharmaceutically acceptable inhibitor of proteolytic enzymes, preferably an inhibitor of proteolytic enzymes of mammalian origin, preferably an inhibitor of proteolytic enzymes of the mammalian gastro intestinal tract, which increases the bioavailability of the active ingredient by a factor of 5, preferably by a factor of at least 6, preferably by a factor of at least 7, preferably by a factor of at least 8, preferably by a factor of at least 9, preferably by a factor of at least 10, whereby the increase in bioavailability of the active ingredient measured in-vivo as relative bioavailability compared to the corresponding or the same formulation but without the proteolytic enzyme inhibitor. Proteolytic enzyme inhibitors include inhibitors of peptidases or proteinases.

The bioavailability promoting agent is different from the penetration promotor. The bioavailability promoting agent is different from cationic (meth)acrylate copolymer comprising tertiary amino groups.

Examples of pharmaceutically suitable protease inhibitors are antipain, aprotinin, bacitracin, benzamidine, bestatin, chymostatin, chicken ovoinhibitor, chitosan-EDTA conjugates, leupeptin, pepstatin, soybean trypsin inhibitors, thiorphan, tos-lys chloromethyl ketone, potato carboxypeptidase inhibitor.

Preferably the inhibitor of proteolytic enzymes is a peptide or a protein. Preferably the peptidase- or proteinase-inhibitor is a peptide or a protein with a molecular weight (weight average $M_w$) of 3.000 to 100.000, preferably 3.000 to 10.000 (g/mol).

An inhibitor of proteolytic enzymes in the sense of the invention inhibits the proteolytic activity of peptidase or proteinases of mammalian origin, such as human trypsin or chymotrypsin. The inhibitor of proteolytic enzymes may be a natural occurring enzyme or derived thereof. Derived from a natural occurring enzyme means fragments or variants thereof. Fragments or variants thereof are available by synthetic processing or modification by gene technological methods.

Preferred the inhibitor of proteolytic enzymes originates from a plant source such as for instance such as soybeans, chickpeas or limabeans. Typical raw materials or sources from which the inhibitor of proteolytic enzymes may be isolated may be soya flours or flakes, chickpea flour, limabean flour or soy whey made from industrial soy protein concentrate or traditional soy protein processes.

The Bowman-Birk inhibitor (BBI) is a well known proteolytic enzyme inhibitor designation of a family of stable low molecular weight trypsin and chymotrypsin inhibitor found in soybeans and various other seeds, mainly in leguminous seeds and vegetable materials. The Bowman-Birk inhibitor (BBI) in the sense of the present invention shall mean at least one or more of the members of Bowman-Birk inhibitor enzyme family.

The proteolytic enzyme inhibitor may be a Bowman-Birk inhibitor or a derivative thereof. The Bowman-Birk inhibitor may be a preferably a soybean derived 71 amino acid polypeptide with distinct inhibitory sides for trypsin and for chymotrypsin. The Bowman Birk inhibitor may be isolated in a known manner from the above mentioned plant sources by aqueous extraction, affinity chromatography and subsequent elution. Alternatively the Bowman-Birk inhibitor is commercially available from different sources.

A derivative of the Bowman-Birk inhibitor may be a fragment or variant thereof. Fragments or variants thereof are available by synthetic processing or by modification for by gene technological methods. The term derivative in this sense is well known to a skilled person.

The concentration by weight of the proteolytic enzyme inhibitor may be preferably 0.1 to 100 fold, preferably 0.5 to 50 fold, preferably 5 to 25 fold, compared to the weight of the active ingredient.

Thus the invention relates to the use of a bioavailability promoting agent which is a pharmaceutically acceptable inhibitor of proteolytic enzymes as an excipient which increases the oral bioavailability of an active ingredient in an inventive formulation.

Increased Oral Bioavailability

The bioavailability promoting agent is a pharmaceutically acceptable inhibitor of proteolytic enzymes, which increases the oral bioavailability of the active ingredient by a factor of at least five, preferably by a factor of at least 6, preferably by a factor of at least 7, preferably by a factor of at least 8, preferably by a factor of at least 9, preferably by a factor of at least 10.

Calculation if Increased Oral Bioavailability

The terms oral bioavailability and the calculation of the relative oral bioavailability are well known to the skilled person.

The factor of increase of the oral bioavailability of the active ingredient may be calculated by dividing the blood level concentration of a test animal group expressed as after under concentration-time curve ($AUC_{0-\infty}$[pg/mL*min]) after oral delivery of the formulation with a corresponding blood level concentration of a corresponding test animal group after oral delivery of a corresponding formulation without the proteolytic enzyme inhibitor. The test animal group shall of course be a representative or respectively a statistical relevant group. A skilled person is familiar with the statistics involved. Thus a representative or a statistical relevant number of test animals can be easily determined by the skilled person. The preferred experimental animal is the minipig (Göttingen). A representative or a statistical relevant group of minipig test animals may consist for instance out of 8 animals (n=8).

The aera under concentration-time curve ($AUC_{0-\infty}$[pg/mL*min]) from the blood of minipigs after oral delivery of desmopressin with the formulation according to example 11 with the inhibitor of proteolytic enzymes is in the present inventive example 16 is 53823 pg/mL*min. This is compared with the $AUC_{0-\infty}$ of the corresponding formulation without the inhibitor of proteolytic enzymes (example 10) which $AUC_{0-\infty}$ is 5155 pg/mL*min. Thus the factor of increase of oral bioavailability is calculated 53823/5155=10.44.

Enteric Coating for the Gastrointestinal Targeted Release of the Active Ingredient At least the cores of the particles or the dosage unit comprise a polymeric coating for the gastrointestinal targeted release of the active ingredient. The polymeric coating for the gastrointestinal targeted release of the active ingredient is an enteric coating respectively an enteric coating layer.

The enteric coating layer may contain up to 50, up to 40, up to 30, up to 20, up to 10% by weight of further excipients like plasticizers or glidants. Preferably the enteric coating layer does not contain essential amounts or any further excipients.

Enteric coatings are well known to the skilled person. Enteric coatings are not soluble in gastric fluids but soluble in enteric fluids. Gastric resistance means that no more than 10% of the active ingredient is released in a buffer of pH 1.2 within 120 min. Soluble in enteric fluids means that they dissolve at a certain pH values between 5.0 and 7.5 depending on their chemical nature in the duodenum, jejunum, ileum or colon.

The polymeric coating for the gastrointestinal targeted release of the active ingredient may comprise carboxyl functional copolymers anionic polysaccharides, cellulosic polymers or anionic (meth)acrylate copolymers.

Suitable carboxyl functional polysaccharides or cellulosic polymers may be selected from sodium alginate, carboxymethyl cellulose and its salts (CMC, Na-CMC, Blanose, Tylopur), carboxymethylethyl cellulose and its salts, cellulose acetate phthalate (CAP), cellulose acetate succinate (CAS), cellulose acetate trimelliate (CAT), hydroxypropyl methyl cellulose phthalate (HPMCP, HP50, HP55), hydroxypropylmethyl cellulose acetate succinate (HPMCAS-LF, -MF, -HF).

Suitable carboxyl functional copolymers are vinyl copolymers comprising structural units that are derived from unsaturated carboxylic acids other than acrylic acid or methacrylic acid as exemplified by polyvinylacetatephthalate or a copolymer of vinylacetate and crotonic acid 9:1.

Anionic(meth)acrylate copolymer

The polymeric coating for the gastrointestinal targeted release of the active ingredient is preferably an anionic (meth) acrylate copolymer. Anionic (meth)acrylate copolymers may be also called enteric polymers. The anionic (meth)acrylate copolymer comprises 25 to 95, preferably 40 to 95, in particular 60 to 40, % by weight free-radical polymerized $C_1$- to $C_4$-alkyl esters of acrylic or of methacrylic acid and 75 to 5, preferably 60 to 5, in particular 40 to 60, % by weight (meth) acrylate monomers having an anionic group.

The proportions mentioned may add up to 100% by weight. However it may also possible in addition, without this leading to an impairment or alteration of the essential properties, that small amounts in the region of 0 to 10, for example 1 to 5, % by weight of further monomers capable of vinylic copolymerization, such as, for example, hydroxyethyl methacrylate or hydroxyethyl acrylate, may be present. However it is preferred that no such further monomers capable of vinylic copolymerization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group is, for example, acrylic acid, with preference for methacrylic acid.

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L 100-55 types).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate 0 to 10% by weight further monomers capable of vinylic copolymerization, where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of 20 to 33, preferably 25 to 32, particularly preferably 28 to 31% by weight methacrylic acid or acrylic acid, with preference for methacrylic acid, 5 to 30, preferably 10 to 28, particularly preferably 15 to 25% by weight methyl acrylate, 20 to 40, preferably 25 to 35, particularly preferably 18 to 22% by weight ethyl acrylate, and more than 10 to 30, preferably 15 to 25, particularly preferably 18 to 22% by weight butyl methacrylate, where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially or exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of anionic(meth)acrylate copolymers

The anionic (meth)acrylate copolymers can be prepared in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of, preferably, anionic emulsifiers, for example by the process described in DE-C 2 135 073.

The copolymer can be prepared by conventional processes of free-radical polymerization continuously or discontinuously (batch processes) in the presence of free-radical forming initiators and, where appropriate, regulators to adjust the molecular weight undiluted, in solution, by bead polymerization or in emulsion. The average molecular weight Mw (weight average, determined for example by measuring the solution viscosity) may be for example in the range from 80 000 to 1 000 000 (g/mol). Emulsion polymerization in aqueous phase in the presence of water-soluble initiators and (preferably anionic) emulsifiers is preferred.

In the case of bulk polymerization, the copolymer can be obtained in solid form by crushing, extrusion, granulation or hot cut.

The (meth)acrylate copolymers are obtained in a manner known per se by free-radical bulk, solution, bead or emulsion polymerization. They must be brought before processing to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Partial Neutralization

Bases suitable for the purposes of the invention are those mentioned in EP 0 088 951 A2 or WO 2004/096185 or derivable there from. Further suitable bases for neutralisation are sodium hydroxide solution, potassium hydroxide solution (KOH), ammonium hydroxide or organic bases such as, for example, triethanolamine, sodium carbonate, potassium carbonate, sodium bicarbonate, trisodium phosphate, trisodium citrate or ammonia or physiologically tolerated amines such as triethanolamine or tris(hydroxymethyl)aminomethane.

Further suitable cationic, organic bases are basic amino acids histidine, arginine and/or lysine.

Adjustment of the Degree of Partial Neutralization by Mixtures

Mixtures may also result in technical advantages in the adjustment of the degree of partial neutralization. In a preferred embodiment of the invention for the inner coating it is made use of mixtures of anionic (meth)acrylate copolymers differing in the degree of partial neutralization, consisting of free-radical polymerized units of 25 to 95% by weight $C_1$- to $C_4$-alkyl esters of acrylic or of methacrylic acid and 5 to 75% by weight (meth)acrylate monomers having an anionic group, wherein 1 to 80% of the contained anionic groups, as calculated average for the mixture, are neutralized by a base. It is possible for example to mix an anionic (meth)acrylate copolymer which is not partially neutralized and consists of free-radical polymerized units of 25 to 95% by weight $C_1$- to $C_4$-alkyl esters of acrylic or of methacrylic acid and 5 to 75% by weight (meth)acrylate monomers having an anionic group with a partially neutralized (meth)acrylate copolymer of the same monomer composition within the stated quantitative ranges so that 1 to 80% of the contained anionic groups, as calculated average for the mixture, are neutralized. The mixture can be prepared for example by stirring a powder which has been obtained from a dispersion of a partially neutralized, anionic (meth)acrylate copolymer, e.g. by spray drying or freeze drying, into a dispersion of an anionic (meth)acrylate copolymer which has not been partially neutralized.

Synchronisation Layer as Part of the Core.

An optional synchronisation layer (sub-coat layer) may be added to the core. The layer has the function of synchronisation of the dissolution the active ingredient and the bioavailability promoting agent. The synchronisation layer may be called as well a sub-coat layer or a separating layer.

A sub-coat layer may have the function to separate substances of the core from substances of the enteric coating layer which may be incompatible with each other. Especially when the penetration promoter in the core is a cationic (meth)acrylate copolymer comprising tertiary amino groups and the outer enteric coating is an anionic cellulosic polymer or an anionic (meth)acrylate copolymer there may be undesired interactions which can be avoided by adding a sub-coat. The sub coat has essentially no influence on the release characteristics. A subcoat is preferably essentially water-soluble, for instance it may consist of substances like hydroxylpropyl methyl cellulose (HPMC) as a film former. The average thickness of the subcoat layer is very thin, for example not more than 50 μm, preferably not more than 30 μm.

The sub-coat layer may comprise at least 50% by weight hydroxypropylmethylcellulose.

The sub-coat layer may comprise up to 90% by weight, preferably up to 50% by weight of the total amount of bioavailability promoting agent in the formulation. If the molecular weight of the active ingredient is lower or much lower than the molecular weight of the bioavailability promoting agent, the active ingredient may diffuse faster out of the core substance than the bioavailability promoting agent.

In this case the active ingredient may reach the target cells without being accompanied by the bioavailability promoting agent. Thus the desired effect may not be reached as it would be if both substances would reach the cells together. Thus the sub-coat layer may preferably comprise up to 90% by weight, preferably up to 50% by weight of the bioavailability promoting agent respectively the inhibitor of proteolytic enzymes. This has the advantage that prior to the release of the active ingredient out of the core at least a small amount of the bioavailability promoting agent out of the rapid dissolving sub-coat may be already on the way to the target cells. This helps to synchronize the release of the active ingredient and of the bioavailability promoting agent (synchronisation layer).

Vice versa the sub-coat layer may comprise up to 20% of the active ingredient. If the molecular weight of the active ingredient is higher or much higher than the molecular weight of the peptidase- or proteinase-inhibitor the active ingredient may diffuse slower out of the core substance than the peptidase- or proteinase-inhibitor. In this case the peptidase- or proteinase-inhibitor may reach the target cells without being accompanied by the active ingredient. Thus the desired effect may not be reached as it would be if both substances would reach the cells together. Thus the sub-coat layer may preferably comprise up to 20% of the active ingredient. This has the advantage that prior to the release of the peptidase- or proteinase-inhibitor out of the core at least a certain amount of the active ingredient out of the rapid dissolving sub-coat may be already on the way to the target cells. This helps to synchronize the active ingredient and the peptidase- or proteinase-inhibitor (synchronisation layer).

The synchronization layer if present may contain up to 50, up to 40, up to 30, up to 20, up to 10% by weight of further excipients. Preferably the synchronization layer does not contain essential amounts or any further excipients.

Production of Multiparticulate Pharmaceutical Forms

The active substance-containing pellet cores can be processed by means of pharmaceutically usual excipients and in a manner known per se to multiparticulate pharmaceutical forms, in particular to pellet-containing tablets, minitablets, capsules, sachets or powders for reconstitution, which are formulated such that the contained pellets are released in the pH range of the stomach. The preparation as multiparticulate pharmaceutical form places high dosage reliability and offers the advantage of uniformly distribution of the pellets in the intestinal lumen. The multiparticulate pharmaceutical form of the invention may additionally also comprise different pellet types with different active substances and/or different pellet structure.

Compressed Tablets

The production of multiparticulate pharmaceutical forms by compression of a pharmaceutically usual binder with active ingredient-containing particles is described for example in Beckert et al. (1996), "Compression of enteric-coated pellets to disintegrating tablets", *International Journal of Pharmaceutics* 143, pp. 13-23, and in WO 96/01624.

Film coatings on active substance-containing pellets are normally applied in fluidized bed apparatuses. Formulation examples are mentioned in this application. Film formers are normally mixed with plasticizers and release agents by a suitable process. It is possible in this case for the film formers to be in the form of a solution or suspension. The excipients for film formation may likewise be dissolved or suspended. Organic or aqueous solvents or dispersing agents can be used. Stabilizers can be used additionally to stabilize the dispersion (example: Tween 80 or other suitable emulsifiers or stabilizers).

Examples of release agents are glycerol monostearate or other suitable fatty acid derivatives, silica derivatives or talc. Examples of plasticizers are propylene glycol, phthalates, polyethylene glycols, sebacates or citrates, and other substances mentioned in the literature.

Mixtures for producing tablets composed of coated particles are prepared by mixing the pellets with suitable binders for tableting, if necessary adding disintegration-promoting substances and if necessary adding lubricants. The mixing can take place in suitable machines. Unsuitable mixers are those leading to damage to the coated particles, e.g. plowshare mixers. To achieve suitable short disintegration times it may be necessary to add the excipients to the coated particles in a specific sequence. It is possible by premixing with the coated particle with the lubricant or mold release agent magnesium stearate for its surface to be rendered hydrophobic and thus for adhesion to be avoided.

Mixtures suitable for tableting normally comprise 3 to 15% by weight of a disintegration aid, e.g. Kollidon CL and, for example, 0.1 to 1% by weight of a lubricant and mold release agent such as magnesium stearate. The proportion of binder is determined by the required proportion of coated particles.

Examples of typical binders are Cellactose®, microcrystalline cellulose, calcium phosphates, Ludipress®, lactose or other suitable sugars, calcium sulfates or starch derivatives. Substances of low bulk density are preferred.

Typical disintegration aids (disintegrants) are crosslinked starch derivatives or cellulose derivatives, and crosslinked polyvinylpyrrolidone. Cellulose derivatives are likewise suitable. It is possible to dispense with the use of disintegration aids through selection of a suitable binder.

Typical lubricants and mold release agents are magnesium stearates or other suitable salts of fatty acids or substances detailed in the literature for this purpose (e.g. lauric acid, calcium stearate, talc, etc.). It is possible to dispense with the use of a lubricant and mold release agent in the mixture on use of suitable machines (e.g. tablet press with external lubrication) or suitable formulations.

It is possible where appropriate to add an aid to the mixture to improve the flow (e.g. colloidal silica derivatives, talc, etc.).

The tableting can take place on usual tablet presses, eccentric or rotary tablet presses, with compressive forces in the range from 5 to 40 kN, preferably 10-20 kN. The tablet presses can be equipped with systems for external lubrication. Special systems for die filling, which avoid die filling by means of impeller paddles, are employed where appropriate.

Further Multiparticulate Pharmaceutical Forms

As an alternative to compressed tablets or minitablets, it is also possible for the active substance-containing coated pellets to be processed to any other orally administered multiparticulate pharmaceutical form. The coated pellets can, for example, be packed into capsules, e.g. gelatin capsules, or formulated to sachets or reconstitutable powders.

Use

The invention further relates to the use of a bioavailability promoting agent which is a pharmaceutically acceptable inhibitor of proteolytic enzymes as an excipient which increases the oral bioavailability of an active ingredient in an inventive formulation. The inventive pharmaceutical or nutraceutical formulation can be applied for human or for veterinary applications.

Nutraceuticals

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or anthocyanins from berries. Sometimes the expression nutraceuticals is used as synonym for nutraceuticals.

Excipients

The core, optionally the synchronization layer and the enteric coating may apart from their essential ingredients include further excipients, which are different from the essential ingredients. The essential ingredients are the active pharmaceutical or nutraceutical ingredient, the penetration promoter, the bioavailability promoting agent and the polymeric coating for the gastrointestinal targeted release of the active ingredient. In the case of a synchronization layer is it of course essential that the layer is formed by a preferably water soluble film forming polymer with a portion of either the active pharmaceutical or neutraceutical ingredient or the bioavailability promoting agent.

The core without the optional synchronisation layer may contain up to 50, up to 40, up to 30, up to 20, up to 10% by weight of further excipients. Preferably the core does not contain essential amounts or any further excipients.

The synchronization layer if present may contain up to 50, up to 40, up to 30, up to 20, up to 10% by weight of further excipients. Preferably the synchronization layer does not contain essential amounts or any further excipients.

The enteric coating layer may contain up to 50, up to 40, up to 30, up to 20, up to 10% by weight of further excipients. Preferably the enteric coating layer does not contain essential amounts or any further excipients.

Pharmaceutical or nutraceutical excipients are well known to the skilled person. Pharmaceutical or nutraceutical excipients may be contained for practical reasons, for instance to avoid stickiness or to add a colour. However these excipients usually do not contribute or do show any or almost no effect on the invention itself as claimed here. They may be used as processing adjuvants and are intended to ensure a reliable and reproducible preparation process as well as good long-term storage stability, or they achieve additional advantageous properties in the pharmaceutical form.

Suitable excipients may be antioxidants, brighteners, binding agents, flavouring agents, flow aids, fragrances, glidants, penetration-promoting agents, pigments, plasticizers, polymers, pore-forming agents or stabilizers. All substances used must of course be toxicologically safe and be used in pharmaceuticals or nutraceuticals without risk for patients.

Plasticizers

Plasticizers achieve through physical interaction with a polymer a reduction in the glass transition temperature and promote film formation, depending on the added amount. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate, propyleneglycol and polyethylene glycols 200 to 12 000. Preferred plasticizers are triethyl citrate (TEC), acetyl triethyl citrate (ATEC), diethyl sebacate and dibutyl sebacate (DBS). Mention should additionally be made of esters which are usually liquid at room temperature, such as citrates, phthalates, sebacates or castor oil. Esters of citric acid and sebacinic acid are preferably used.

Addition of the plasticizers to the formulation can be carried out in a known manner, directly, in aqueous solution or after thermal pre-treatment of the mixture. It is also possible to employ mixtures of plasticizers.

Glidants/Release Agents/Detackifiers:

Glidants, release agents or detackifiers usually have lipophilic properties and are usually added to spray suspensions. They may be added to the core formulation or to the enteric coating. They prevent agglomeration of cores during film formation or agglomeration of the coated pellets. Examples are talc, Mg- or Ca-stearate, ground silica, kaolin or nonionic emulsifiers with an HLB value of between 2 and 8. Standard proportions for use of glidants in the inventive coating and binding agents range between 0.5 and 70 wt % relative to the weight of the cores or relative to the weight of the enteric coating.

Data Calculations

Calculations were performed using the MS Excel spreadsheet package.

Apparent Permeability Coefficient ($P_{app}$)

The $P_{app}$ was calculated according to Eq. 1.

$$P_{app} = \frac{\Delta Q}{\Delta t} \cdot \frac{1}{m_0} \cdot \frac{1}{A} \cdot V_D [cm \cdot s^{-1}] \qquad \text{Eq. 1}$$

$\Delta Q/\Delta t$ permeability rate (steady state transport rate) obtained from the profile of the transported amount of substrate versus time [µg or dpm·s$^{-1}$]. Calculated by the linear regression of time and concentration A area of the exposed cell monolayer [cm$^2$]

$m_0$ initial mass of test compound in the donor compartment [µg or dpm]

$V_D$ buffer volume of donor compartment [cm$^3$]

Transepithelial Electrical Resistance (TEER)

The TEER was calculated according to Eq. 2.

$$\text{TEER} = R_{c(A)} = (R_{c+f} - R_f) \cdot A [\Omega \cdot cm^2] \qquad \text{Eq. 2}$$

$R_{c(A)}$ electrical resistance of the monolayer with the area A [$\Omega \cdot cm^2$]

$R_{c+f}$ electrical resistance of the monolayer including the filter [$\Omega$]

$R_f$ electrical resistance of the filter without cells [$\Omega$]

A area of monolayer [cm$^2$]

The electrical resistance of a cell free filter with an area of 1.13 cm$^2$ is 100 $\Omega$.

Flux

The Flux was calculated according to Eq. 3.

$$\text{Flux} = \frac{c_{Ak120}}{c_{D0}} \cdot 100 [\% \text{ of donor}] \qquad \text{Eq. 3}$$

$c_{AK120}$ Concentration of API [µg·mL$^{-1}$] in the acceptor after 120 min $c_{D0}$ Concentration of API [µg·mL$^{-1}$] in the donor at the beginning of the experiment (0 min)

EXAMPLES

Materials

EUDRAGIT® E is a copolymer composed of 25% by weight of methyl methacrylate, 25% by weight of butyl methacrylate and 50% by weight of dimethylaminoethyl methacrylate. EUDRAGIT® E PO is the powder form of EUDRAGIT® E with an average particle size of about 15 µm.

EUDRAGIT® L 30 D-55 is a dispersion comprising 30% by weight EUDRAGIT® L 100-55. EUDRAGIT® L 100-55 is a copolymer of 50% by weight ethyl acrylate and 50% by weight methacrylic acid.

Minirin® is a commercially available desmopressin acetate containing medicine in the form of tablets. One Minirin® tablet weighs 200 mg and contains a nominal content of 200 µg desmopressin.

Bowman-Birk inhibitor (BBI) from soy bean source was used (Sigma Aldrich, Germany)

Heparin: Low molecular weight heparin (LMW-Heparine); Fraxiparin™ (Nadroparin calcium); Glaxo Smith Kline Preparation Examples 1 to 11

Example 1

As desmopressin preparation for example 1 commercially available tablets containing desmopressin were used (Minirin®)

Minirin control formulation was obtained by mixing one Minirin® tablet together with cellets (microcrystalline cellulose pellets) in order to obtain a weight equal to the other desmopressin formulations.

One Minirin® tablet (200 mg containing a nominal content of 200 µg desmopressin) was cut into halves. These pieces were mixed with Cellets® 500 (microcrystalline cellulose pellets) in order to achieve a total weight of 350 mg.

Example 2

Preparation of Pellets of Desmopressin and EUDRAGIT® E PO as Penetration Promotor The formulation of example 2 was manufactured in two steps. The first step is the preparation of the spray coating solution. The second step is the application of the spray coating solution in a spray coating process. In this way EUDRAGIT® E/desmopressin pellets with a particle size fraction 400-710 µm were obtained.

Preparation of a Spray Solution 83 g EUDRAGIT® E PO were filled into a 1000 ml glass beaker. During mechanical stirring at 700 rpm the total amount of 1N HCl and 90% of the total amount of water was added into the polymer dispersion. After stirring constantly 10 min, 8.3 g Tween® 80 were added to the dispersion. A clear solution with medium viscosity and a slight foam formation was obtained after further stirring of 1 h at 850 rpm. After filtration of the HCl neutralized EUDRAGIT® E PO solution through a 0.315 mm wire mesh, the Desmopressin solution was added. The whole solution was stirred further 10 min to obtain a uniform mixture.

Manufacturing of Desmopressin/EUDRAGIT® E PO Pellets by Spray Coating Process

Starting material for the preparation of the desmopressin/EUDRAGIT® E PO cores was 50 g of non-pareilles sugar pellets fraction 250-355 µm. On this, 591.3 ml of HCl neutralized EUDRAGIT® EPO solution containing desmopressin was applied by spray coating.

In short, the process has been run as follow:

The inlet air was adjusted to 35-51° C. and the product temperature was set to 29-35° C. The spraying speed was started with 0.3 to 2.5 g solution/min and the airflow was kept from 16 to 20 m³/h. The spraying process was finished after 327 min. At the end the pellets were dried in the machine for 10 min sieved through a 710 µm sieve. The final yield obtained was 139.77 g corresponding to 95% of the theoretical weight.

Example 3

Preparation of Pellets of Desmopressin, EUDRAGIT® E PO as Penetration Promotor and Bowman-Birk Inhibitor (BBI)

The formulation of example 3 was manufactured in two steps. The first step is the preparation of the spray coating solution. The second step is the application of the spray coating solution in a spray coating process. In this way EUDRAGIT® E/desmopressin/BBI pellets with a particle size fraction 400-710 µm were obtained.

Preparation of a Spray Solution 189.9 g EUDRAGIT® E PO were filled into a 1000 ml glass beaker. Under mechanical stirring at 600 rpm, 16.31 g of Sodium dodecylsulfate dissolved in 60% of the total amount of water was added to the polymer. After stirring constantly for 10 min, 182.7 g Acetic acid solution 10% were added slowly into the beaker to avoid coagulation of the polymer. 30 min later the total amount of molten capric acid was added into the mixture. A clear solution with medium viscosity and a slight foam formation was obtained after further stirring of 2 h at 850 rpm. 25.31 g Bowman Birk inhibitor (BBI) and the remaining amount of Sodium dodecylsulfate were dissolved in 190.4 g of water using a 250 ml glass bottle and added into the polymer solution during stirring. Desmopressin was dissolved in 10% of the remaining water using a 50 ml glass beaker. After filtration of the neutralized EUDRAGIT® E PO solution through a 0.315 mm wire mesh, the desmopressin solution was added. The whole solution was stirred further 10 min to obtain homogeneity in the mixture.

Manufacturing of Desmopressin/EUDRAGIT® E PO/BBI Pellets by Spray Coating Process Starting material for the preparation of the desmopressin/EUDRAGIT® E PO/BBI cores was 50 g of non pareil sugar pellets fraction 250-355 µm.

The process has been run as follow:

The inlet air was adjusted to 40-48° C. and the product temperature was set to 29-33° C. The spraying speed was started with 0.8 to 4.0 g solution/min and the airflow was kept from 16 to 27 m³/h. The spraying process was finished after 314 min. At the end the pellets were dried in the machine for 10 min sieved through a 710 µm sieve. The final weight obtained was 146.15 g corresponding to 77% of desmopressin/EUDRAGIT® E PO/BBI pellets 400-710 µm of total weight of desmopressin/EUDRAGIT® E PO/BBI pellets.

Example 4

Preparation of Pellets from Example 2 with an Additional HPMC Coating Layer

The pellets from example 2 were taken and further coated with HPMC. In a first step the HPMC spray coating solution is prepared. In a second step the HPMC spray coating solution was applied to the pellets in a spray coating process. In this way EUDRAGIT® E/desmopressin pellets with a HPMC coating with a particle size fraction 400-710 µm were obtained.

Preparation of HPMC Spray Solution 252.8 g of water were filled into a 250 ml glass bottle and heated up to about 70° C. under stirring using a magnetic stirrer. The total amount of 25 g hydroxypropylmethylcellulose was added gradually to the hot water. After stirring constantly for 15 min, the solution was removed from the heater and was cooled till room temperature. Lost water by evaporation was filled up. The HPMC solution was filtered through a 0.315 mm wire mesh.

Manufacturing of Desmopressin/EUDRAGIT® E PO Pellets with HPMC Coating

Starting material for the preparation of the of the coated pellets was 100 g of sieved pellets of example 2, fraction <600 µm. On this, 277.8 g of the HPMC spray coating solution were applied by spray coating.

The process was carried out as follows: The product temperature was set to 29-35° C. by adjusting an inlet air temperature of 30° C. at the beginning increasing to 55° C. at the end of the process depending on the process air humidity. The spraying was started with 0.7 to 1.4 g solution/min and the airflow was set from 12 to 16 m³/h. The spraying process was finished after 215 min. The pellets were dried 10 min at 10 m³/h and 34 to 35° C. product temperature using the spray coater and then sieved through a 600 µm sieve. The final weight obtained was 122.99 g corresponding to 98% of coated pellets <600 µm of total theoretical expected weight.

Example 5

Preparation of Pellets from Example 3 with an Additional HPMC Synchronisation Layer Containing BBI The pellets from example 3 were taken and further coated with HPMC containing BBI. In a first step the HPMC/BBI spray coating solution is prepared. In a second step the HPMC/BBI spray coating solution was applied to the pellets in a spray coating process. In this way EUDRAGIT® E/desmopressin/BBI pellets with a HPMC/BBI coating with a particle size fraction 400-710 µm were obtained.

Preparation of HPMC Spray Solution Containing BBI 178 g of water was filled into a 250 ml glass bottle and heated up to about 70° C. during stirring using a magnetic stirrer. The total amount of 19.5 g HPMC was added gradually to the hot water. After stirring constantly for 15 min, the solution was removed from the heater and was cooled till room temperature. Lost water by evaporation was filled up. 2.6 g Bowman Birk inhibitor (BBI) was dissolved in 45.5 g water using a 50 ml glass beaker. After filtration of the clear HPMC solution through a 0.315 mm wire mesh the BBI solution was added. The whole solution was stirred further 15 min to obtain homogeneity in the mixture.

Manufacturing of Desmopressin/EUDRAGIT® E PO/BBI Pellets with HPMC/BBI Coating 130 g of sieved pellets from example 3, fraction 500-710 µm were used as starting material. On this, 245.6 ml of the HPMC/BBI coating solution were applied by spray coating.

The process was carried out as follows: The inlet air was adjusted to 30-45° C. and the product temperature was set to 29-33° C. The spraying speed was started with 0.6 and raised to 2.2 g solution/min and the airflow was kept from 18 to 24 m³/h. The spraying process was finished after 134 min. At the end the pellets were dried in the machine for 10 min sieved through a 710 µm sieve and the yield was checked by weighing. The final weight obtained was 149.23 g corresponding to 98% of coated pellets <710 µm of total theoretical expected weight.

Example 6

Preparation of Pellets from Example 4 with an Additional EUDRAGIT® L 30 D-55 Enteric Coating Layer The pellets from example 4 were taken and further coated with EUDRAGIT® L30D-55. In a first step the EUDRAGIT® L30D-55 spray coating solution is prepared. In a second step the EUDRAGIT® L30D-55 spray coating solution was applied to the pellets in a spray coating process. In this way EUDRAGIT® E/desmopressin pellets with a HPMC coating and EUDRAGIT® L30D-55 enteric coating with a particle size fraction 400-710 µm were obtained.

Preparation of EUDRAGIT® L30D-55 Spray Dispersion

Into a 100 ml glass bottle 105 g of water was filled and heated up to about 80° C. under stirring with a magnetic stirrer. After increasing the magnetic stirrer speed, 3.6 g of Tween 80 solution (33.33%) were added to the hot water before adding 3.0 g glycerol monostearate. After stirring vigorously for 15 min, the dispersion was taken away from the heater and cooled during vigorously stirring till room temperature. Lost water by evaporation was filled up.

133.3 g sieved EUDRAGIT® L 30 D-55 dispersion and 72.4 g of water were mixed in a 250 ml glass bottle. Under stirring 4 g of triethyl citrate were added into the dispersion. After further stirring of 10 min, the prepared glycerol monostearate dispersion mentioned above was added. The whole dispersion has been stirred further 40 min to obtain homogeneity in the spray solution.

Manufacturing of Enteric Coated Pellets from Example 4

Starting material for the preparation of the coated pellets was 100 g of sieved pellets of example 4, fraction <600 µm. On this, 321.3 g of the EUDRAGIT® L30D-55 spray dispersion were applied by spray coating.

The process was carried out as follows: The product temperature was set to 30-36° C. by adjusting an inlet air temperature of 37° C. at the beginning increasing to 52° C. at the end of the process depending on the process air humidity. The spraying process was started with 0.6 increasing to 2.6 g solution/min and the airflow was set from 16 m³/h at the beginning to 18 m³/h. The spraying process was finished after 213 min. The pellets were dried 10 min at 10 m³/h and 35 to 36° C. product temperature using the spray coater and then sieved through a 710 µm sieve. The pellets were further dried additionally 2 h at 40° C. in a drying oven. The final weight obtained was 145.03 g corresponding to 98% of coated pellets <710 µm of the total theoretical expected weight.

Example 7

Preparation of Pellets from Example 5 with an Additional EUDRAGIT® L 30 D-55 Enteric Coating Layer The pellets from example 5 were taken and further coated with EUDRAGIT® L30D-55. In a first step the EUDRAGIT® L30D-55 spray coating solution is prepared. In a second step the EUDRAGIT® L30D-55 spray coating solution was applied to the pellets in a spray coating process.

In this way EUDRAGIT® E/desmopressin/BBI pellets with a HPMC/BBI coating and EUDRAGIT® L30D-55 enteric coating with a particle size fraction 400-710 μm were obtained.

Preparation of EUDRAGIT® L30D-55 Spray Dispersion 52.5 g of water was filled into a 100 ml glass bottle and heated up to about 80° C. under stirring with a magnetic stirrer. 1.8 g of Tween 80 solution (33.33%) was added to the hot water stirring the dispersion vigorously before adding 1.5 g glycerol monostearate. After 15 min stirring vigorously, the dispersion was taken away from the heater and was cooled during vigorously stirring till room temperature. Lost water of evaporation was filled up. 66.7 g sieved EUDRAGIT® L 30 D-55 dispersion and 36.2 g of water were mixed into a 250 ml glass bottle. Under stirring 2 g of Triethyl citrate was added into the dispersion. After further stirring of 10 min, the prepared glycerol monostearate dispersion mentioned above was added. The whole suspension has been stirred further 40 min to obtain homogeneity in the spray solution.

Manufacturing of Enteric Coated Pellets from Example 5

Starting material for the preparation of the coated pellets was 100 g of sieved pellets of example 4, fraction <710 μm. On this, 160.7 ml of the above described EUDRAGIT® L30D-55 spray dispersion were applied by spray coating.

The inlet air was adjusted to 35-46° C. and the product temperature was set to 30-33° C. The spraying speed was started with 0.3 and raised to 1.6 g solution/min and the airflow was kept from 16 to 18 m$^3$/h. The spraying process was finished after 146 min. The pellets then were dried in the machine for 10 min sieved through a 710 μm sieve and the yield was checked by weighing. The final weight obtained was 123.98 g corresponding to 100% of coated pellets <710 μm of the total theoretical expected weight.

Example 8

Drug Control (Capsule)

The pellets of example 1 were filled into a HPMC capsule size 1.

The mixtures of example 1 were filled into a HPMC capsule size 1 using a filling funnel in order to achieve a total weight of 350 mg. The uniformity of capsule weight was 350.2 mg+/−0.9 (standard deviation, n=10). The content uniformity of desmopressin in the capsules was 215.62+/−5.55 μg (standard deviation, n=10).

Example 9

Non-Inventive Formulation (Capsule)

The pellets of example 2 were filled into a HPMC capsule size 1.

For one capsule 107 mg pellets of example 2, with a content of about 205 μg desmopressin, were mixed with Cellets® 500 as filling material to fill HPMC size 1 capsules with a total weight of 350 mg. The uniformity of capsule weight was 350.5 mg+/−0.3 (standard deviation, n=10). The content uniformity of desmopressin in the capsules was 204.57+/−2.42 μg (standard deviation, n=10).

Example 10

Non-Inventive Formulation (Capsule)

The pellets of example 6 were filled into a HPMC capsule size 1.

For one capsule 195.6 mg pellets of example 6, with a content of about 225 μg desmopressin, were mixed with Cellets® 500 as filling material to fill HPMC size 1 capsules with a total weight of 350 mg. The uniformity of capsule weight was 350.1 mg+/−0.2 (standard deviation, n=10). The content uniformity of desmopressin in the capsules was 225.4+/−0.51 μg (standard deviation, n=10).

Example 11

Inventive Formulation (Capsule)

The pellets of example 7 were filled into a HPMC capsule size 1.

For one capsule 145.5 mg pellets of example 7, with a content of about 211 μg desmopressin, were mixed with Cellets® 500 as filling material to fill HPMC size 1 capsules with a total weight of 350 mg. The uniformity of capsule weight was 350.0 mg+/−0.2 (standard deviation, n=10). The content uniformity of desmopressin in the capsules was 211.31+/−1.19 μg (standard deviation, n=10).

Test examples 12 to 16

Example 12

TEER

In-Vitro Test of the Preparations of Examples 1, 4 and 5 in CacoII-Cells (TEER-Values)

Preparation of CacoII-Cell-Monolayers for Transepithelial Electrical Resistance (TEER) Measurements For the transport experiments, Caco-2 cells were seeded with a density 60,000 cells per square centimeter on Transwell™ filter inserts, which were placed into 12-well flat bottom cluster plates. The inserts (apical compartments) were supplied with 0.5 mL and the outer wells (basal compartments) with 1.5 mL of DMEM culture medium. The cells were cultured at 37° C., 10% $CO_2$ and 90% relative humidity in DMEM culture medium for 14 to 30 days until they formed confluent monolayers. The culture medium was replaced every 2-3 days. Confluency and tightness of the cell monolayer was routinely checked by measuring the transepithelial electrical resistance using an EVOM™ voltohmmeter.

A Caco-2 monolayer batch is defined as Caco-2 cells seeded and cultured in parallel under the same conditions on Transwell™ filters. Qualification of Caco-2 monolayer batches by means of selected transport markers is performed in triplicate for each transport condition. The following quality criteria have to be fulfilled before a monolayer batch is released for permeability studies:

Caco-2 passage number less than 50

Culture age 14 to 30 days on Transwell™ filters

TEER values before and after transport above 200 Ω·cm$^2$ (indicating integrity and tightness of the cell monolayer)

Apparent permeability coefficient (ab and ba) of a low permeable marker (Fluorescein) less than $1 \cdot 10^{-6}$ cm·s$^{-1}$ (indicating suitability of the model to identify low permeable transport, assuring tightness of the cell monolayer).

Apparent permeability coefficient (ba) of Rhodamine 123 higher than $4 \cdot 10^{-6}$ cm·s$^{-1}$ (indicating evident expression of P-glycoprotein)

Apparent permeability coefficient (ab) of Propranolol higher than $5 \cdot 10^{-6}$ cm·s$^{-1}$ (indicating suitability of the model to identify high permeable transport)

The following quality criteria have to be fulfilled for each individual monolayer used for the permeability studies with the test compounds:

Monolayers are part of a qualified batch.

TEER must be higher than 200 Ω·cm$^2$ after pre-incubation (30-45 min), otherwise the monolayer is rejected TEER should be higher than 200 Ω·cm$^2$ after the transport study, lower TEER values indicate a lack of the monolayer's integrity over the study Buffers Used in the Experiments for the Apical or for the Basolateral Side

TABLE 1

| HBSS buffer pH 6.5 (apical side) | | HBSS buffer pH 7.4 (basolateral side) | |
|---|---|---|---|
| Compound | Conc. [mM] | Compound | Conc. [mM] |
| MgSO$_4$ | 0.812 | MgSO$_4$ | 0.812 |
| CaCl$_2$ | 0.952 | CaCl$_2$ | 0.952 |
| NaCl | 136.7 | NaCl | 136.7 |
| KCl | 5.36 | KCl | 5.36 |
| Na$_2$HPO$_4$•2 H$_2$O | 0.385 | Na$_2$HPO$_4$•2 H$_2$O | 0.385 |
| K$_2$HPO$_4$•3 H$_2$O | 0.441 | K$_2$HPO$_4$•3 H$_2$O | 0.441 |
| Glucose | 25 | Glucose | 25 |
| MES | 10 | HEPES | 10 |

The pH was adjusted by NaOH/HCl

Preparation and Measurement of Samples

For the experiments 1 mg of the Minirin® powdered tablets of example 1 or intact pellets from examples 4 and 5 were applied to the donor compartment. As a further control a mixture of desmopressin acetate and Cellets® 700 were applied.

The effect of the pellet formulation on the TEER was evaluated by TEER monitoring during the transport experiment. The TEER was measured at 0, 15, 30, 60, 120 and 240 min. After the last TEER measurement, the content of the apical compartment and basolateral was removed and the cells were washed and recultivated in cell culture medium for additional 20 h. The TEER was measured again to evaluate the reversibility of the permeation enhancement.

Results

TABLE 2

| | Example | | | | | | | |
|---|---|---|---|---|---|---|---|---|
| | 1 | | 4 | | 5 | | Control Cellets ® with desmopressin | |
| Time [h] | Mean-TEER [%] | SD | Mean-TEER [%] | SD | Mean-TEER [%] | SD | Mean-TEER [%] | SD |
| Medium | 79 | 9 | 84 | 2 | 82 | 1 | 79 | 9 |
| HBSS | 100 | 0 | 100 | 0 | 100 | 0 | 100 | 0 |
| 0 min | 103 | 6 | 27 | 1 | 92 | 3 | 103 | 6 |
| 15 min | 81 | 3 | 15 | 1 | 25 | 3 | 81 | 3 |
| 30 min | 82 | 2 | 14 | 1 | 17 | 1 | 82 | 2 |
| 60 min | 85 | 4 | 15 | 1 | 14 | 1 | 85 | 4 |
| 120 min | 82 | 2 | 15 | 1 | 12 | 2 | 82 | 2 |
| 240 min | 70 | 1 | 11 | 1 | 10 | 1 | 64 | 3 |

The TEER values of the pellets from examples 4 and 5 were reduced to less than 15% compared to the buffer control. In contrast to this the formulation from example 1 showed only a reduction to 70%.

Example 13

Flux

In-Vitro Test of the Preparations of Examples 1, 4 and 5 in CacoII-Cells (Flux Measurements)

Preparation of CacoII-Cell-Monolayers for Flux Measurements

Caco-II-cell monolayers were prepared in the same way as in example 12

Preparation and Measurement of Samples

A solution of Desmopressin acetate containing 1000 μg·mL$^{-1}$ was prepared in HBSS buffer pH 6.5 by dissolving 10 mg substance in 10 ml buffer.

The solution was and applied to the donor compartment together with 1 mg of the pellet formulation, or the powdered Minirin tablet.

For the experiments 1 mg of the Minirin® powdered tablet of example 1 or intact pellets from examples 4 and 5 were applied to the donor compartment. As a further control a mixture of desmopressin acetate and Cellets® 700 were applied.

As no pre-incubation was performed the concentration of test compound found in the transport solution was taken as initial donor concentration ($c_{D0}$). After 120 minutes samples of 100 μL were taken from the acceptor compartments and the donor compartments. Between the sampling points, the monolayers were incubated at 37° C. in a CO$_2$ incubator. All experiments were performed in triplicate.

As a control inert pellets (cellets) were used.

The solution were analysed by HPLC using a RP-18-column as a stationary phase and a water/acetonitrile-mixture (80:20) as eluent phase at a wavelength of 220 nm. The Flux was calculated as percentage of 1000 μg·ml$^{-1}$ desmopressin with represents the 100% amount applied at th donor side. The desmopressin content in the pellets applied (ca. 2 μg) was neglected for the calculation.

Results

The results of the "Flux" experiments are summarized in table 3.

TABLE 3

| Transport | Flux [in % of D$_0$] | SD (standard deviation, n = 3) |
|---|---|---|
| Control: Desmopressin acetate + Cellets 700 700-1000 μm | 0.18 | 0.82 |
| Desmopressin acetate + Formulation from example 4 | 24.24 | 5.89 |
| Desmopressin acetate + Formulation from example 5 | 20.36 | 6.76 |
| Desmopressin acetate + formulation from example 1 (powdered Minirin ® tablets) | 0.22 | 0.02 |

As a result it becomes evident that formulations from examples 4 and 5 increase the Flux of desmopressin in CacoII-cells to a value of more than 20%.

Example 14

Proteolytic Enzyme Inhibition

In-Vitro Pancreatic Enzyme Inhibition Test of the Preparations of Examples 1, 4 and 5

Experimental Design

Inhibition experiments were performed using a new study design considering the dissolution of the pellets.

80 mg of each formulation were stirred in 10 ml of HBSS pH 5.8 at the lowest stirring speed available. The stirring was stopped after 30 min and the suspensions allowed to settle down before an aliquot (2 ml) was drawn and mixed with 2 mL of a solution containing 80 $\mu g \cdot ml^{-1}$ of Desmopressin acetate in HBSS buffer pH 6.5. The pH of the solutions was measured but not adjusted.

As a negative control 2 ml of HBSS buffer were mixed with 2 ml of a solution containing 80 $\mu g \cdot ml^{-1}$ of Desmopressin acetate in HBSS buffer pH 6.5. The pH of the solutions was measured but not adjusted.

As a positive control a solution containing 4 mg of BBI per ml in HBSS was used. 2 ml of the solution were mixed with 2 ml of a solution containing 80 $\mu g \cdot ml^{-1}$ of Desmopressin acetate in HBSS buffer pH 6.5. The pH of the solutions was measured but not adjusted.

200 µL of the prepared solutions were mixed with 200 µl of a Pancreatin solution (20 $mg \cdot ml^{-1}$) and incubated for 1, 2 and 3 h at 37° C. Each experiment was performed in triplicate (three individually prepared solutions).

(Final concentrations in the positive control: 1 mg/ml BBI, 20 µg/ml desmopressin actuate and 10 mg/ml pancreatin)

For the 100% value 80 mg pellets were stirred in 10 ml HBSS pH 5.8 for 30 min and homogenized using an ultraturrax. The suspension was stirred for further 15 minutes and allowed to settle down.

The supernatant was collected and further diluted with Desmopressin acetate in HBSS buffer pH 6.5 as described above. The pH of the solutions was measured but not adjusted.

For the starting values ($t_0$) the mixture was directly added to 400 µl of acetonitrile and diluted with 1200 µL of HBSS buffer pH 6.5. The solution were analysed by HPLC using a RP-18-column as a stationary phase and a water/acetonitrile-mixture (80:20) as eluent phase at a wavelength of 220 nm.

Results

The results of the enzyme inhibition experiments are summarized in table 4.

TABLE 4

| Time (min) | 0 | 60 | 120 | 180 |
|---|---|---|---|---|
| Negative Control (desmopressin in HBSS buffer) | 100.00 | 61.79 | 50.51 | 33.54 |
| RSD % | — | 18.34 | 6.05 | 10.63 |
| Pellets from example 4 homogenized | 100.00 | 65.51 | 46.56 | 38.54 |
| RSD % | — | 4.57 | 7.29 | 14.94 |
| Supernatant from pellets from example 4 after 30 min released | 100.00 | 68.74 | 45.12 | 33.06 |
| RSD % | — | 7.56 | 20.37 | 27.59 |
| Pellets from example 5 homogenized | 100.00 | 90.87 | 79.54 | 64.62 |
| RSD % | — | 8.23 | 3.29 | 6.63 |
| Supernatant from pellets from example 5 after 30 min released | 100.00 | 85.98 | 76.16 | 61.56 |
| RSD % | — | 5.05 | 2.80 | 5.47 |
| Minirin ® tablets homogenized (example 1) | 100.00 | 65.48 | 50.07 | 33.40 |
| RSD % | — | 8.84 | 10.70 | 1.24 |
| Supernatant from Minirin ® tablets from example 1 after 30 min released | 100.00 | 69.08 | 51.44 | 39.63 |
| RSD % | — | 9.41 | 5.71 | 15.33 |
| Positive Control BBI (ca. 4-fold concentrated than in example 5) | 100.00 | 98.82 | 94.48 | 85.25 |
| RSD % | — | 3.09 | 5.06 | 1.84 |

RSD = relative standard deviation, n = 3

Results obtained for formulations and controls (n=3). The tablet formulation (Minirin®) and pellet from example 4 showed almost no inhibitory properties, the degradation kinetics is similar to the negative control (buffer). Almost no difference was observed between dissolved (30 minutes) and homogenized samples. Only the positive control and the pellets from example 5 could remarkably reduce the degradation of desmopressin acetate by pancreatin. However, even in the absence of the BBI a recovery of more than 60% of desmopressin is observed. This indicates that the effect of the BBI is detectable but marginal.

Example 15

Synchronisation

In-Vitro Test of the Preparations of Examples 5, 7 and 11 for Synchronisation of Desmopressin and Bowman-Birk Inhibitor Dissolution tests of pellets have been carried out according to USP apparatus 2 at 37° C., paddle speed 100 rpm, phosphate buffer pH 6.0, n=6, 1 g per vessel according to about 1400-2100 µg desmopressin acetate. Additionally the enteric pellets were treated 2 h in Hydrochloric acid, 0.1N, before switching at pH 6.0.

Dissolution tests of capsules have been carried out in the same way, n=6, 5 capsules per vessel corresponding to a total of 1080 µg desmopressin acetate.

Collected samples were analyzed using a HPLC were desmopressin and BBI were measured separately with UV detection at 210 nm.

Results

The synchronisation effect is shown in tables 5, 6 and 7 in percentage of the total amount of each substance.

Dissolution Profile of Pellets from Example 5 in Phosphate Buffer pH 6.0 Shown Individually for Desmopressin and for BBI

TABLE 5

| Zeit [min] | Example 5 desmopressin | Example 5 BBI |
|---|---|---|
| 0 | 0.74 | 1.8 |
| 10 | 77.3 | 73.2 |
| 20 | 94.8 | 90.5 |

TABLE 5-continued

| Zeit [min] | Example 5 desmopressin | Example 5 BBI |
| --- | --- | --- |
| 30 | 97.3 | 97.7 |
| 40 | 98.8 | 98.8 |
| 43 | 100 | 100 |

Dissolution Profile of Pellets from Example 7 after 2 h HCl 0.1N and Changing to pH 6.0 Shown Individually for Desmopressin and for BBI

TABLE 6

| Zeit [min] | Example 7 Desmopressin | Example 7 BBI |
| --- | --- | --- |
| 0 | 0.7 | 2.7 |
| 60 | 0.7 | 2.7 |
| 120 | 0.7 | 2.7 |
| 130 | 96.2 | 95.8 |
| 140 | 97.7 | 97.2 |
| 150 | 98.2 | 98.3 |
| 160 | 98.7 | 98.6 |
| 210 | 99.1 | 98.8 |
| 213 | 100 | 100 |

Dissolution Profile of Capsules from Example 11 after 2 h HCl 0.1N and Changing to pH 6.0 Shown Individually for Desmopressin and for BBI

TABLE 7

| Zeit [min] | Example 11 Desmopressin | Example 11 BBI |
| --- | --- | --- |
| 0 | 1.1 | 4.5 |
| 60 | 1.1 | 4.5 |
| 120 | 1.1 | 4.5 |
| 130 | 93.3 | 95.8 |
| 140 | 93.41 | 98.2 |
| 150 | 95.21 | 99.1 |
| 160 | 96.4 | 99.1 |
| 210 | 98.5 | 98.3 |
| 213 | 100 | 100 |

The dissolution profile of pellets from examples 5 and 7 and of capsules from example 11 show a fast (>90% after 20 min) and complete (nearly 100% after 30 min) release at pH 6.0 of desmopressin and BBI in a synchronized matter. The deviation at this time points (20/30 min in example 5 or 140/150 min in examples 7 and 11) is less than 5%.

Example 16

In-Vivo Study

In Vivo Test of the Preparations of Examples 8, 9, 10 and 11 in Minipigs (Relative Bioavailability)
Method Description Minipigs were selected as being a good model to study oral bioavailability in man. The minipigs are smaller than domestic pigs and are therefore easier to handle.

Species: Minipig (Göttingen)
Source: Ellegaard Göttingen Minipigs A/S (Dalmose, DK)
Number, Sex: 8 males; no extra animals were included. No unforeseen complication arose with any of the animals.
Age, body weight: The animals were 7-8 months old at the time of dosing with an average body weight of 12 kg. Upon arrival at TNO the animals were weighed and allocated in two groups. One day prior to each dosing session, the animal weights were recorded.

Acclimatization: The animals were acclimatized to the laboratory conditions, the biotechnical staff and the dosing and sampling procedure by daily training on week days for 3 weeks prior to the start of the study.

Health condition: Upon arrival, the animals were taken to a quarantine room and checked for overt signs of ill health and anomalies. The quarantine room was subsequently cleared for use as experimental room.

Environment: The animals were housed under conventional conditions in one room. No other test system was housed in the same room during the study. The room was ventilated with about 10 air changes per hour and maintained at a temperature of 22° C.+/−2° C. and a relative humidity of at least 40% and not exceeding 70% other than during room cleaning Lighting was artificial with a sequence of 12 hours light and 12 hours dark.

Housing: During acclimatization and during the study, the animals were housed in pens with straw as bedding and toys, 4 minipigs per pen. On blood collection days the animals were housed individually. During the second week of dosing, the animals began to fight with each other and were therefore housed individually from then on in order to avoid bite wounds.

Identification: The animals were ear tagged with a unique number by the supplier. They kept this tag throughout the study. The animals were also numbered from 1 to 8 by a number written on the forehead.

Diet: The minipigs were fed twice a day around 350 g of a commercial minipig diet (Mpig-H). Each batches of this diet is analyzed by the supplier (Ssniff Spezialdiaten GmbH, Soest, Germany) for nutrients and contaminants. Analysis certificates pertaining to the batch used in this study are included in the study files.

Drinking water: Drinking water was offered ad libitum. The drinking water was suitable for human consumption.
Test Formulations Capsules from examples 8, 9, 10 and 11 were used for the studies
Content: ca. 215 µg desmopressin per capsule
Storage conditions: +2 to +8° C.
Stability: stable under storage conditions
Experimental Procedures The animals received a single dose of each formulation (1 capsule) and blood samples were taken after each dosing.
Animals 1-4 received the four formulations in the following order: Capsules from examples 9, 10,11 and 8.
Animals 5-8 received the same formulations in reverse order.

This procedure (cross-over study) allows accounting for possible undesirable effects of the repeated dosing of desmopressin (e.g. antibody production) on parameters governing its own pharmacokinetics or unaccounted effects of the formulations (e.g. effect on the intestinal functions).
Dose Level, Administration, Group Size and Identification The dose level has been selected by ca. 215 µg desmopressin acetate absolute as based on a body weight of 70 kg in man. Each group comprised 4 male minipigs. The animal numbers assigned to the treatment groups have been recorded during the study to allow a clear group identification.

The test item was administered orally to each animal on the basis of 1 capsule containing the corresponding amount of test substance. Oral administration was performed by placing a bite stick (perforated in its centre) between the teeth of the animals. A pill gun equipped with a tubing (of approximately 0.5 cm diameter) was inserted through the hole in the mouth of the minipig and the capsule was shot directly in the throat. The bite stick was removed after the animal had swallowed.

The animals were given access to freshly tapped drinking water immediately after dosing.

Each formulation was given once only and each dosing was followed by a wash-out period of one week.

Blood Collection

Blood samples of approximately 0.5 ml each were collected from the jugularis vein of each animal at 15, 30, 45, 60, 90, 120, 180, 240, 360, 480 minutes after each dosing, by alternating sides per session in order to allow the sampling site to recover between two sampling sessions.

Samples were collected into Vacationers containing K2EDTA. The tubes were centrifuged at +4° C. (3000 rpm for 10 minutes) within 30 minutes after collection and the plasma collected in two aliquots (A and B) into polyethylene tubes. The plasma samples were stored frozen at <−70° C. until shipment on dry ice to the site of analysis.

Each sample was identified by study number, animal code, sample type, sampling date sampling time.

Bioanalysis:

The plasma samples were analysed for desmopressin concentration by a RIA method.

Pharmacokinetic Analysis and Statistics

The results of the bioanalysis were analysed by using KineticaR v4.2. The plasma concentration versus time curves were constructed from the definitive results and analysed by non-compartmental analysis.

The following pharmacokinetic parameters were calculated where the data allowed:

Cmax, Tmax, the terminal half-life (T1/2), the volume of distribution (Vz), the total clearance (ClT), the Area under the concentration-time curve ($AUC_{0-\infty}$).

The relative bioavailability was calculated as the ratio between the average $AUC_{0-\infty}$ of capsules from example 8 (Minirin®) and the $AUC_{0-\infty}$ of the formulations of examples 9, 10 and 11 respectively.

The results have been expressed as total area under the curve and as percentage and reported in table 8.

TABLE 8

| | Example 9 | Example 10 (Control formulation, corresponding to inventive example 11) | Example 11 Inventive formulation | Example 8 drug control |
|---|---|---|---|---|
| Aera under concentration-time curve $AUC_{0-\infty}$ [pg/mL*min] | 4467 | 5155 | 53823 | 7573 |
| Relative bioavailability $AUC_{0-\infty}$ [%] to drug control | 59 | 68 | 711 | 100 |
| Relative bioavailability $AUC_{0-\infty}$ [%] to formulation control | 87 | 100 | 1044 | 147 |
| Increase in bioavailabilty factor | — | — | 10.44 | — |

The examples 9 and 10 were not better than the reference example 8 (Minirin®, drug control), presenting a relative bioavailability of around 59 and 68% compared to drug control.

However the examples 9 and 10 can be considered in a comparable range as the drug control example 8 which is based on a commercially available product.

In contrast, the formulation of example 11 presented a seven times higher relative bioavailability $AUC_{0-\infty}$ (711%) than the drug control example 8 (100%).

The increase in oral bioavailability as claimed is calculated by comparison of example 11 with example 10. The aera under concentration-time curve ($AUC_{0-\infty}$[pg/mL*min]) from the blood of minipigs after oral delivery of desmopressin with the formulation according to example 11 with the inhibitor of proteolytic enzymes is 53823 pg/mL*min. This is compared with the $AUC_{0-\infty}$ of the corresponding formulation without the inhibitor of proteolytic enzymes (example 10) which $AUC_{0-\infty}$ is 5155 pg/mL*min (=100%). Thus the factor of increase of oral bioavailability is calculated 53823/5155=10.44 (=1044%).

The pellets contained in the capsules from examples 8, 9, 10 and 11 corresponding to the pellets of examples 1, 4, 6 and 7 respectively. The formulations 6 and 7 represent the enteric coated pellets of examples 4 and 5 respectively.

The pellets of examples 4 and 5 gave good cell penetration effects in in-vitro cell assays shown in examples 12 and 13 (TEER and Flux values). The formulations from examples 4 and 5 increased the Flux of desmopressin in CacoII-cells to a value of more than 20%. The TEER values of the pellets from examples 4 and 5 were reduced to less than 15% compared to the buffer control. In contrast to this the formulation from example 1 (Minrin®) showed only a reduction to 70%.

However the promising results of the pellets of example 4 which are placed in the capsules of examples 9 and 10, without or with enteric coating respectively, obtained in-vitro lead only to disappointing results in-vivo. When the corresponding formulations were tested in-vivo in minipigs, only pour bioavailability could be detected. This was less than the value obtained for the capsule of example 8 which contains the reference preparation of example 1 (drug control).

Only the capsule formulation from example 11 (containing the pellets from example 7, which is the enteric coated version of the example 5 pellets) which as the only one contained the bioavailability promoting agent BBI showed a clear increase bioavailability by a factor of 10.44, when compared to the example 10 control formulation which is the corresponding formulation to inventive formulation of example 11.

This strong increase of the relative bioavailability can not be explained merely by the only weak effect of the enzyme inhibition activity of BBI shown in example 14.

Due to the fact that the in-vivo effect was so much higher compared to the in-vitro results the inventors believe that this effect can not be explained merely by the protective effect of the proteolytic enzyme inhibitor against the pancreatic enzymes. Furthermore there seems to be a new unknown effect that increases the bioavailability of active ingredients caused by the addition of a proteolytic enzyme inhibitor in general or at least by such one from plant origin or at least by the Bowman-Birk inhibitor (BBI) in combination with the other elements of the system as claimed.

Example 17

TEER, Pure Penetration Promotor

The penetration promoter in the sense of the present invention may be defined by reducing the initial TEER-value of the buffer solution without penetration promotor (100%) to 50% or less, preferably 40% or less, preferably 30% or less, preferably 20% or less in the presence of the penetration promotor at a concentration of 1 mg/ml after 60 min measured in a Caco-2-cell monolayer culture as transport barrier.

TEER-Testing was performed analogous to example 12. EUDRAGIT® E acetate=EUDRAGIT® E dissolved in water by addition of acetic acid until clear solution was obtained; EUDRAGIT® E PO base=dispersion of EUDRAGIT® E PO (powder form of EUDRAGIT® E) in water (not dissolved); chitosan acetate=chitosan dissolved in water by addition of acetic acid until clear solution was obtained.

TABLE 9

| | Substance | | | | | | | | | |
|---|---|---|---|---|---|---|---|---|---|---|
| | Negative Control (HBSS buffer pH 7.4) | | EUDRAGIT ® E acetate 0.005% | | EUDRAGIT ® E PO base 0.005% | | Chitosan acetate 0.005% | | Positive Control (Sodium dodecylsufate 0.1%) | |
| Time [h] | Mean-TEER [%] | SD* | Mean-TEER [%] | SD | Mean-TEER [%] | SD | Mean-TEER [%] | SD | Mean-TEER [%] | SD |
| HBSS (0 min) | 100 | 0 | 100 | 0 | 100 | 0 | 100 | 0 | 100 | 0 |
| 5 min | 75 | 4 | 35 | 2 | 40 | 0 | 63 | 10 | 12 | 2 |
| 60 min | 71 | 4 | 23 | 3 | 27 | 7 | 42 | 5 | 4 | 0 |
| 120 min | 80 | 2 | 23 | 3 | 22 | 6 | 30 | 9 | 10 | 2 |
| 180 min | 84 | 5 | 22 | 1 | 24 | 6 | 23 | 5 | 12 | 3 |
| 240 min | 90 | 6 | 22 | 4 | 23 | 6 | 20 | 3 | 15 | 2 |

*SD = standard deviation;
n = 3

EUDRAGIT® E acetate, EUDRAGIT® E base and chitosan acetate fulfil the TEER requirement for penetration promotor since they reduce TEER to less than 50% after 60 min even at a concentration of 0.005%=0.05 mg/ml (below 1 mg/ml).

Example 18

TEER, Cationic Penetration Promotor/Anionic Active Ingredient

TEER-Testing was performed analogous to example 12.

TABLE 10

| | TEER in % of TEER in Medium during the test (mean of n = 3) | | | | | | | | |
|---|---|---|---|---|---|---|---|---|---|
| | Example-No. | | | | | | | | |
| | 18a | 18b | 18c | 18d | 18e | 18f | 18g | 18h | 18i |
| | Formulation | | | | | | | | |
| Time [min] | Desmo E/BBI | Desmo BBI | Desmo | Heparin | Heparin/E/BBI (4:1) | Heparin/E/BBI (1:1) | Heparin/E/BBI (0.25:1) | 0.1% SDS | HBSS |
| buffer | 120 | 117 | 123 | 118 | 139 | 126 | 121 | 123 | 124 |
| 0 | 27 | 111 | 119 | 110 | 139 | 123 | 119 | 22 | 132 |
| 15 | 18 | 101 | 111 | 102 | 130 | 118 | 109 | 16 | 129 |
| 30 | 20 | 105 | 115 | 106 | 132 | 119 | 108 | 16 | 130 |
| 60 | 15 | 104 | 111 | 105 | 126 | 123 | 117 | 12 | 135 |
| 90 | 15 | 111 | 118 | 112 | 109 | 130 | 120 | 16 | 138 |
| 120 | 11 | 109 | 119 | 111 | 46 | 133 | 120 | 12 | 139 |
| 240 | 11 | 98 | 109 | 104 | 26 | 118 | 121 | 13 | 139 |

Description of the Formulations:
The following mixtures in HBSS-buffers were tested
Abbreviations:
Desmopressin acetate=Desmo,
EUDRAGIT® E Carbonate=E (s. description: carbonated amino(meth)acrylate copolymer)
Bowman Birk Inhibitor=BBI
Heparin: Low molecular weight heparin (LMW-Heparine); Fraxiparin™ (Nadroparin calcium); 0.6 ml ready to use syringe for subcutaneous injection (5700 IU anti-Xa/mg); Ch.B.: 3394-1; Glaxo Smith Kline Example 18a Desmo 0.01%/E 0.1%/BBI 0.01%

Example 18b

Desmo 0.01%/BBI 0.01%

Example 18c

Desmo 0.01% (active ingredient control)

Example 18d

Heparin 0.1% (active ingredient control)

Example 18e

Heparin 0.1%/E 0.4%/BBI 0.01%

Example 18f

Heparin 0.1%/E 0.1%/BBI 0.01%

Example 18g

Heparin 0.1%/E 0.25%/BBI 0.01%

Example 18h

Sodiumdodecylsufate (SDS) 0.1% (positive control)

Example 18i

HBSS-buffer (negative control)
Discussion of the Results:

Examples 18a, 18e, 18f and 18g are representing the qualitative composition of the core of the inventive formulations (without gastrointestinal coating). Examples 18a and 18e are effective in reduction of TEER-values, whereas examples 18f and 18g are not.

Example 18a shows strong TEER value reduction which is due to the presence of EUDRAGIT® E which becomes apparent from comparative examples 18b and 18c without EUDRAGIT® E or without EUDRAGIT® E and BBI respectively.

In the examples 18e, 18f and 18g heparin is used as an example for a strong anionic active ingredient. In these examples heparin is mixed with the cationic EUDRAGIT® as penetration promotor and BBI. In the examples 18f and 18g there is no reduction of TEER. This is supposed to be due to an excess of anionic heparin which interferes which the cationic penetration promotor activity and inhibits its functionality. In example 18e a delayed reduction of TEER is observed. This is supposed to be due to an excess of the cationic penetration promotor activity over the anionic heparin, so that the penetration promotor activity is not fully inhibited as in example 18f and 18g. The examples 18e, 18f and 18g show that loss of penetration promotor activity may occur when the anionic and the cationic substances are mixed together in amounts which are approximately equimolar in respect to their charges or where the active ingredient is present in access over the penetration promoter. This can be overcome for instance by increasing the total amount of penetration promoter over the active ingredient as shown in example 18e.

The invention claimed is:

1. A pharmaceutical or nutraceutical formulation, comprising:
    a core, comprising an active pharmaceutical or nutraceutical ingredient, a penetration promoter, a bioavailability promoting agent, and only one synchronization layer; and
    a polymeric coating suitable for gastrointestinal targeted release of the active ingredient,
    wherein the penetration promoter is a copolymer comprising from 30 to 80% by weight of at least one $C_1$- to $C_4$-alkyl ester of acrylic or of methacrylic acid, and from 70 to 20% by weight of at least one alkyl(meth)acrylate monomer having a tertiary amino group in an alkyl radical,
    wherein the bioavailability promoting agent is a pharmaceutically acceptable inhibitor of a proteolytic enzyme, and
    the bioavailability promoting agent is configured to increase oral bioavailability of the active ingredient by a factor of at least five, compared to a corresponding formulation without the bioavailability promoting agent.

2. The formulation of claim 1, wherein the inhibitor of proteolytic enzymes is a Bowman-Birk inhibitor.

3. The formulation of claim 1, wherein the active ingredient has a low permeability according to Biopharmaceutical classification system (BCS)-classes III and IV.

4. The formulation of claim 1, further comprising:
    an inhibitor capable of preventing or reducing enzymatical degradation of the active ingredient,
    wherein the active ingredient is of biological origin.

5. The formulation of claim 1, wherein the active ingredient is a protein, a peptide, a lipid, a polysaccharide, or nucleic acid.

6. The formulation of claim 1, wherein the active ingredient is desmopressin, desmopressin acetate or desmopressin lactate.

7. The formulation of claim 1, wherein the formulation is a multiparticulate pharmaceutical or nutraceutical formulation comprising a multitude of particles in one dosage unit.

8. The formulation of claim 7, comprising from 10 to 1000 particles.

9. The formulation of claim 7, wherein the particles have sizes of from 0.2 to 2 mm.

10. The formulation of claim 1, wherein an amount of the bioavailability promoting agent in the formulation is from 0.1 to 10% by weight.

11. The formulation of claim 1, wherein the penetration promoter is a cationic polymeric substance.

12. The formulation of claim 1, wherein up to 90% by weight of the bioavailability promoting agent is the synchronization layer.

13. The formulation of claim 1, wherein the polymeric coating comprises an anionic cellulosic polymer or an anionic (meth)acrylate copolymer.

14. The formulation of claim 1,
    wherein the active ingredient is anionic,
    the penetration promoter is cationic, and
    the active ingredient and the penetration promoter avoid ionic interaction by an excessive amount of the penetration promoter in a mixture of both the active ingredient and the penetration promoter in one compartment of the formulation; by local separation of both the active ingredient and the penetration promoter in different compartments of the formulation; or by inclusion of a salt, an amphiphilic polymer, a hydrogen bonding non-ionic polymer, or a combination thereof in a mixture of both the active ingredient and the penetration promoter in one compartment of the formulation.

15. The formulation of claim 1, wherein the penetration promoter is a copolymer consisting of 30 to 80% by weight of at least one $C_1$- to $C_4$-alkyl ester of acrylic or of methacrylic acid, and from 70 to 20% by weight of at least one alkyl(meth)acrylate monomer having a tertiary amino group in an alkyl radical.

16. The formulation of claim 1, wherein the active ingredient is heparin or derivative thereof.

17. A method of increasing oral bioavailability of an active ingredient in a formulation, the method comprising:
    including a bioavailability promoting agent in a core of a formulation in need thereof,
    wherein the bioavailability promoting agent is a pharmaceutically acceptable inhibitor of proteolytic enzymes
    the core further comprises the active ingredient, only one synchronization layer, and a penetration promoter,
    the active ingredient is a pharmaceutical or nutraceutical ingredient,
    the formulation further comprises a polymeric coating suitable for gastrointestinal targeted release of the active ingredient, and
    the bioavailability promoting agent is configured to increase oral bioavailability of the active ingredient by a factor of at least five, compared to a corresponding formulation without the bioavailability promoting agent.

* * * * *